(12) United States Patent
Lim et al.

(10) Patent No.: US 11,619,546 B2
(45) Date of Patent: Apr. 4, 2023

(54) SENSING MODULE AND VITAL SIGN MEASURING DEVICE INCLUDING THE SAME

(71) Applicant: SAMSUNG ELECTRONICS CO., LTD., Suwon-si (KR)

(72) Inventors: Jungwook Lim, Hwaseong-si (KR); Seungki Jung, Bucheon-si (KR)

(73) Assignee: SAMSUNG ELECTRONICS CO., LTD., Suwon-si (KR)

( * ) Notice: Subject to any disclaimer, the term of this patent is extended or adjusted under 35 U.S.C. 154(b) by 349 days.

(21) Appl. No.: 16/869,731

(22) Filed: May 8, 2020

(65) Prior Publication Data

US 2021/0131864 A1    May 6, 2021

(30) Foreign Application Priority Data

Nov. 5, 2019 (KR) .................. 10-2019-0140446

(51) Int. Cl.
*A61B 5/00* (2006.01)
*G01R 31/52* (2020.01)
*G01J 1/44* (2006.01)

(52) U.S. Cl.
CPC .............. *G01J 1/44* (2013.01); *A61B 5/0059* (2013.01); *G01R 31/52* (2020.01); *A61B 2562/0233* (2013.01); *A61B 2562/046* (2013.01); *G01J 2001/444* (2013.01)

(58) Field of Classification Search
CPC .......... A61B 5/0059; A61B 2562/0233; A61B 2562/146; G01J 1/44; G01J 2001/444; G01R 31/52
See application file for complete search history.

(56) References Cited

U.S. PATENT DOCUMENTS

| 2016/0183818 A1 | 6/2016 | Richards et al. |
| 2018/0177413 A1 | 6/2018 | Kwon et al. |
| 2018/0263519 A1 | 9/2018 | Gu |
| 2019/0191120 A1* | 6/2019 | Ikedo ................. H04N 5/37452 |

FOREIGN PATENT DOCUMENTS

| JP | 5376768 B2 | 12/2013 |
| KR | 10-1620334 B1 | 5/2016 |
| KR | 10-1780061 B1 | 10/2017 |
| KR | 10-1898067 B1 | 9/2018 |

* cited by examiner

*Primary Examiner* — Minh Q Phan
(74) *Attorney, Agent, or Firm* — Sughrue Mion, PLLC

(57) ABSTRACT

A sensing module is provided. The sensing module includes a light source, unit pixels, a leakage current detector, and a pixel driving circuit. The light source outputs an optical signal. The unit pixels are connected to row lines and column lines, and sense the optical signal to generate a pixel signal. The leakage current detector compares an amplitude of the pixel signal generated by the unit pixels with a first reference voltage, in a state in which the light source is deactivated, to detect a unit pixel, among the unit pixels, in which a leakage current equal to or greater than a threshold value is generated. The pixel driving circuit deactivates the detected unit pixel in a state in which the light source is activated.

20 Claims, 22 Drawing Sheets

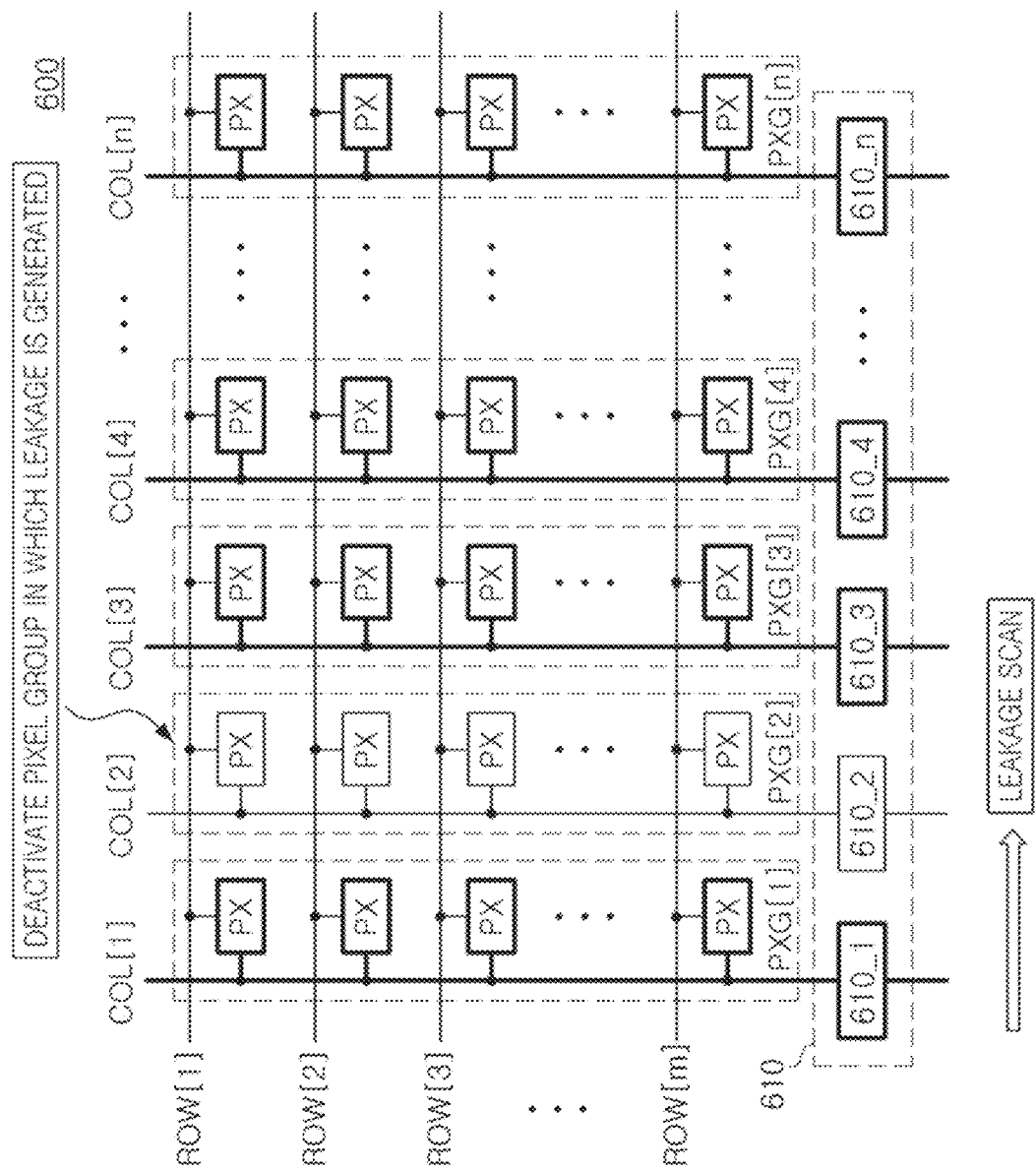

SENSING MODULE AND VITAL SIGN MEASURING DEVICE INCLUDING THE SAME

CROSS-REFERENCE TO RELATED APPLICATION(S)

This application claims priority from Korean Patent Application No. 10-2019-0140446 filed on Nov. 5, 2019 in the Korean Intellectual Property Office, the disclosure of which is incorporated by reference herein in its entirety.

BACKGROUND

1. Field

The present disclosure relates to a sensing module and a vital sign measuring device including the same.

2. Description of the Related Art

Recently, demand for an electronic device equipped with healthcare functions is continuously increasing. Accordingly, a vital sign measuring device capable of measuring various vital signs such as a user's heart rate, blood oxygen saturation (e.g., $SpO_2$), or the like, has been in the spotlight. The vital sign measuring device is an electronic device, and is required to minimize a size and power consumption thereof. In order to satisfy these requirements, research into a device and a method for measuring a vital sign using an image sensor has been actively conducted.

SUMMARY

It is an aspect to provide a sensing module capable of deactivating a unit pixel, in which a leakage current equal to or greater than a threshold value occurs, in a predetermined unit, and a vital sign measuring device including the same.

According to an aspect of an embodiment, there is provided a sensing module comprising a light source that outputs an optical signal; a plurality of unit pixels that are connected to a plurality of row lines and a plurality of column lines, and that sense the optical signal to generate a pixel signal; a leakage current detector that compares an amplitude of the pixel signal generated by the plurality of unit pixels with a first reference voltage, in a state in which the light source is deactivated, to detect a unit pixel, among the plurality of unit pixels, in which a leakage current equal to or greater than a threshold value is generated; and a pixel driving circuit that deactivates the detected unit pixel in a state in which the light source is activated.

According to another aspect of an embodiment, there is provided a sensing module comprising a plurality of unit pixels that are connected to a plurality of row lines and a plurality of column lines, the plurality of unit pixels being grouped in a predetermined unit to form at least one pixel group; a first leakage current detector that is connected to an output node of the at least one pixel group, respectively, and that compares an amplitude of a pixel signal generated at the output node of the at least one pixel group with a reference voltage, to detect a pixel group in which a leakage current equal to or greater than a threshold value is generated; and a second leakage current detector that activates the plurality of unit pixels row line by row line, wherein the first leakage current detector compares an amplitude of a pixel signal at the output node of the detected pixel group that is generated by each of the plurality of unit pixels activated by the second leakage current detector with the reference voltage, to detect a unit pixel included in the detected pixel group, in which the leakage current has occurred, and wherein the detected unit pixel in which the leakage current has occurred is deactivated in a turned-on state of a light source.

According to another aspect of an embodiment, there is provided a vital sign measuring device comprising at least one light source that outputs an optical signal; a sensing module that includes a pixel array including a plurality of unit pixels that detect a reflected optical signal reflected from an object to generate a pixel signal, and a pixel driving circuit that generates a vital sign of the object from the pixel signal; and a light shielding film that optically separates the sensing module from the at least one light source, wherein the sensing module detects a unit pixel, among the plurality of unit pixels, in which a leakage current has occurred, and applies a control signal to deactivate the detected unit pixel.

According to another aspect of an embodiment, there is provided a sensing module comprising a light source that outputs an optical signal; a plurality of unit pixels that sense the optical signal to generate a pixel signal, the plurality of unit pixels being arranged in rows and columns and being arranged by columns into a plurality of pixel groups; a first leakage current detector that, in a state in which the light source is deactivated, compares an amplitude of the pixel signal at an output node of each pixel group with a reference voltage to detect a pixel group in which a leakage current equal to or greater than a threshold value is generated; and a pixel driving circuit that deactivates at least one unit pixel included in the detected pixel group in a state in which the light source is activated

BRIEF DESCRIPTION OF DRAWINGS

The above and other aspects will be more clearly understood from the following detailed description, taken in conjunction with the accompanying drawings, in which:

FIGS. 10A and 10B are views illustrating an operation of a sensing module according to the method of FIG. 9, according to an embodiment;

DETAILED DESCRIPTION

Figure 1:
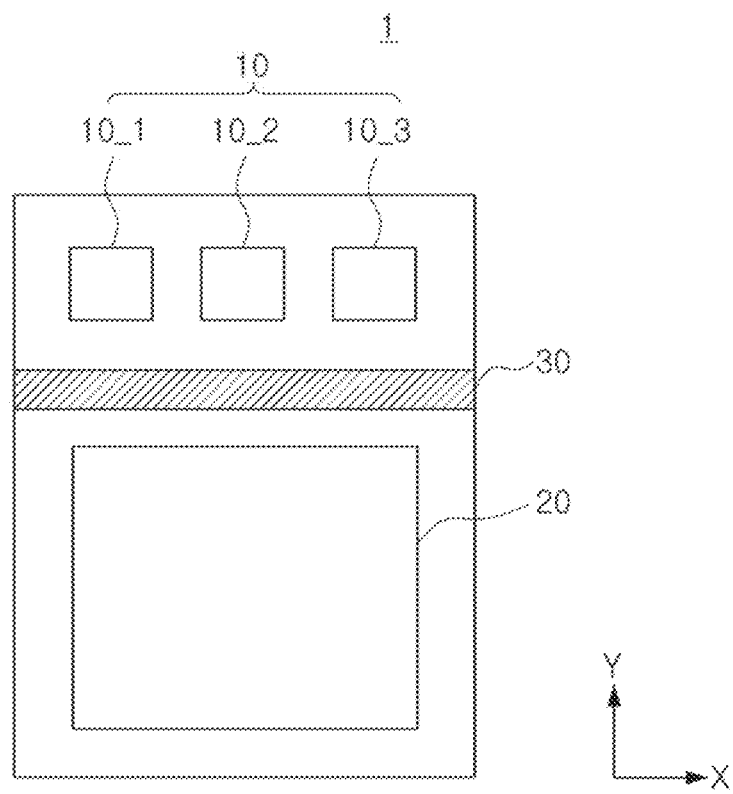
FIGS. 1 and 2 are views schematically illustrating a structure of a vital sign measuring device according to an embodiment.

Hereinafter, various embodiments will be described in detail with reference to the accompanying drawings. The same reference numerals may be used for the same components in the drawings, and duplicate descriptions of the same components will be omitted for conciseness.

Figure 2:
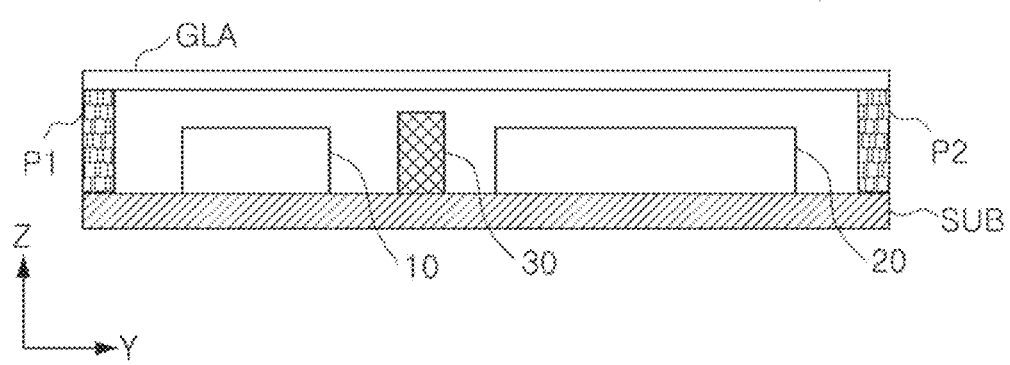

FIGS. 1 and 2 are views schematically illustrating a structure of a vital sign measuring device according to an embodiment. FIG. 1 illustrates a vital sign measuring device viewed in a direction parallel to a substrate (e.g., on an X-Y plane), and FIG. 2 illustrates a vital sign measuring device viewed in a direction perpendicular to a substrate (e.g., on a Y-Z plane).

Referring to FIG. 1, a vital sign measuring device 1 may include at least one light source 10 and a sensing module 20, arranged on a substrate, and a light shielding film 30 configured to separate the light source 10 and the sensing module 20 in a direction parallel to the substrate.

When the vital sign measuring device 1 receives a vital sign measuring request, the vital sign measuring device 1 may turn on the light source 10 to output an optical signal. In some embodiments, the vital sign measuring request may be received from a user. However, this is only an example, in in some embodiments, the vital sign measuring request may be received from another device or from a component within the vital sign measuring device 1.

The light source 10 may include at least one individual light source 10_1 to 10_3. Although FIG. 1 illustrates that the light source 10 includes three individual light sources 10_1 to 10_3, embodiments are not limited thereto. In some embodiments, the light source 10 may have fewer or more than three individual light sources.

The individual light sources 10_1 to 10_3 may each include at least one light emitting device. For example, the individual light sources 10_1 to 10_3 may include a light emitting diode (LED), a laser diode, a vertical cavity surface emitting laser (VCSEL), a phosphor, or the like. A plurality of light emitting devices included in the individual light sources 10_1 to 10_3 may be arranged in an array form.

The sensing module 20 may detect an optical signal scattered or reflected by a biological tissue (e.g., a blood vessel) of an object, and generate a vital sign of the object from the detected optical signal.

The sensing module 20 may include a pixel array including a plurality of unit pixels configured to detect the optical signal and to generate an electrical signal from the detected optical signal, and a pixel driving circuit configured to generate the vital sign of the object by using the electrical signal generated by the plurality of unit pixels. In an embodiment, the vital sign of the object may include a photoplethysmogram (PPG) signal, an electrocardiogram (ECG) signal, an electromyography (EMG) signal, or the like. The object may be a body region of a user. The object may contact or be adjacent to the vital sign measuring device 1, and may be a body part from which a vital sign is easily capable of being generated. For example, when a photoplethysmogram PPG signal is measured by using the vital sign measuring device 1, the object may be a body part of a user having a relatively thin skin tissue and a relatively high blood vessel density, such as a wrist, an ear, or the like.

In a turned-off state of the light source 10, a leakage current may occur in the pixel array of the sensing module 20, and the leakage current exceeding a threshold value may greatly reduce sensing accuracy of the vital sign measuring device 1. The threshold value may be predetermined. Therefore, the sensing module 20 according to an embodiment may deactivate a unit pixel in which the leakage current is generated, to improve the sensing accuracy of the vital sign measuring device 1. The sensing module 20 may deactivate a pixel group including the unit pixel in which the leakage current is generated, to minimize the power consumption of the vital sign measuring device 1.

Referring to FIG. 2, a light source 10 and a sensing module 20 may be arranged on a substrate SUB, and may be arranged to be spaced apart from each other and to be separated from each other by a light shielding film 30 in a direction parallel to the substrate SUB (e.g., in a Y-axis direction in FIG. 2).

A vital sign measuring device 1 may further include a light transmitting plate GLA disposed above the light source 10 and the sensing module 20. The light transmitting plate GLA may extend in a direction parallel to the substrate SUB (e.g., in a Z-axis direction). The light transmitting plate GLA may be supported by a plurality of support portions P1 and P2 that are arranged on the substrate SUB and that extend in a direction perpendicular to the substrate SUB as shown in FIG. 2. The light transmitting plate GLA may form an appearance of the vital sign measuring device 10 together with the plurality of support portions P1 and P2. In an embodiment, the light transmitting plate GLA may include a transparent material such as acrylic, indium tin oxide (ITO), or the like.

An optical signal output from the light source 10 may be emitted to an outside of the vital sign measuring device 1 through the light transmitting plate GLA. An optical signal reflected from an object may re-enter the inside of the vital sign measuring device 1 through the light transmitting plate GLA. The optical signal that re-enters into the inside of the vital sign measuring device 1 may be detected by the sensing module 20, and may be used to measure the vital sign of the object.

The light shielding film 30 may prevent the optical signal output from the light source 10 from being directly transmitted to the sensing module 20 without passing through the GLA, in order to remove noise components included in the vital sign and improve sensing accuracy. In an embodiment, the light shielding film 30 may include an opaque material such as silicon oxide, a metal material, or the like.

Hereinafter, the sensing module 20 included in the vital sign measuring device 1 will be described in more detail with reference to the accompanying drawings.

Figure 3:
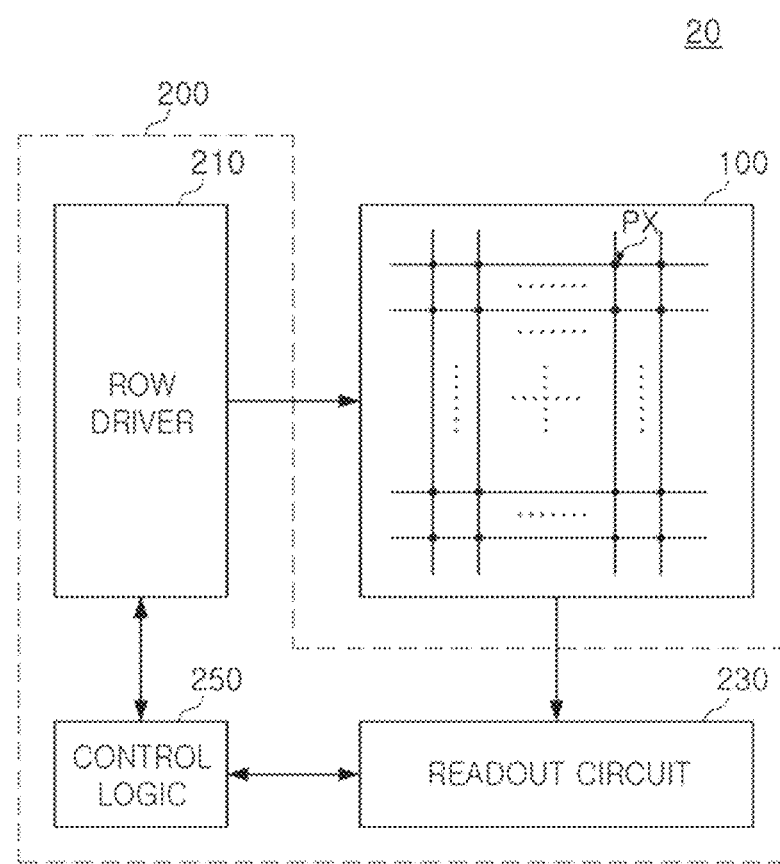
FIG. 3 is a view illustrating a sensing module of the vital sign measuring device of FIGS. 1-2, according to an embodiment.

FIG. 3 is a view illustrating the sensing module 20 of the vital sign measuring device 1 of FIGS. 1-2, according to an embodiment.

Referring to FIG. 3, the sensing module 20 may include a pixel array 100 and a pixel driving circuit 200. The pixel driving circuit 200 may include a row driver 210, a readout circuit 230, and a control logic 250, which will be described in more detail later.

The pixel array 100 may include a plurality of unit pixels PX. When the plurality of unit pixels PX are arranged in a matrix form, the unit pixels PX may be arranged at points at which a plurality of row lines and a plurality of column lines intersect.

Figure 4A:
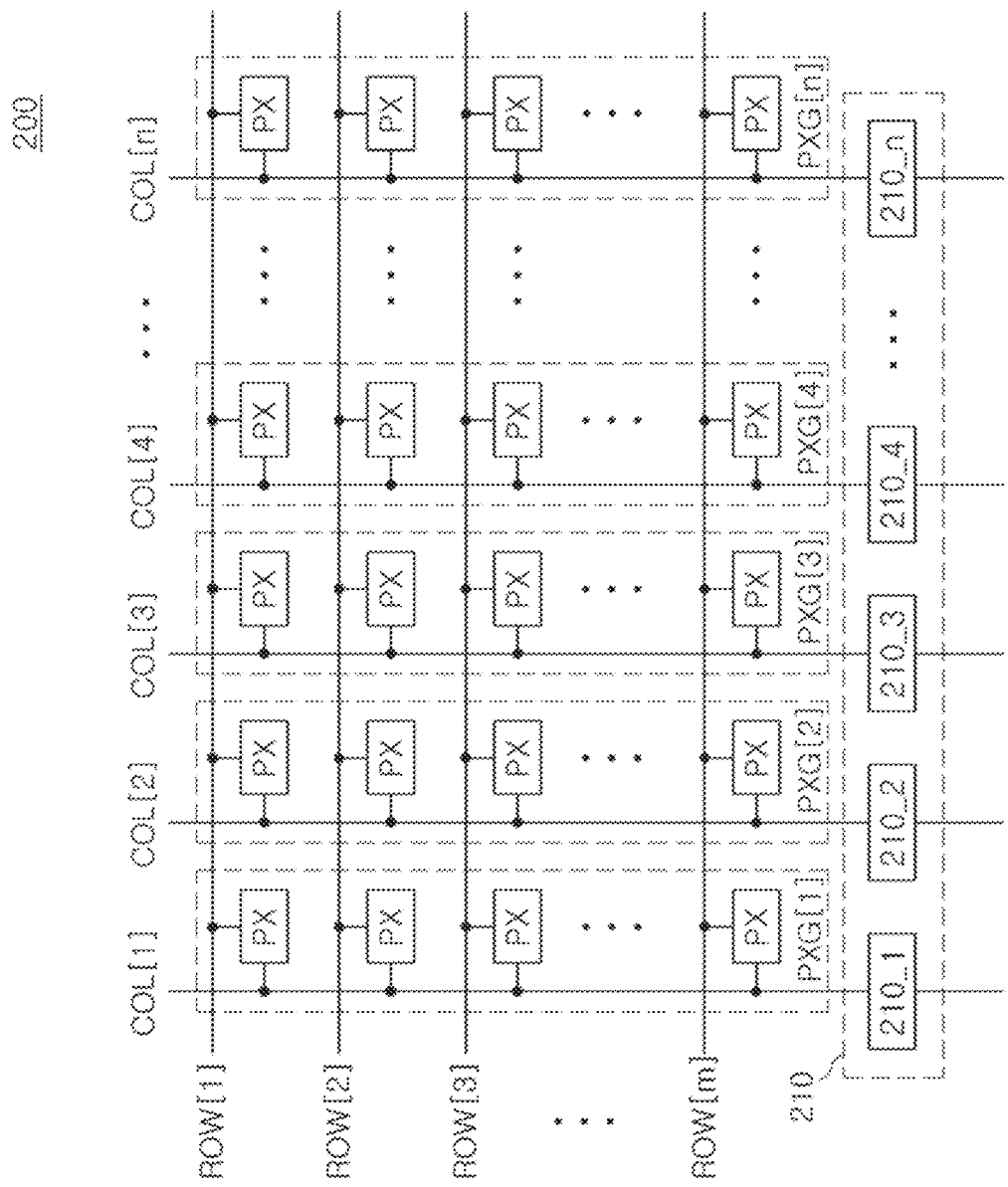
FIGS. 4A and 4B are views illustrating a pixel array included in the sensing module of FIG. 3, according to various embodiments.
Figure 4B:
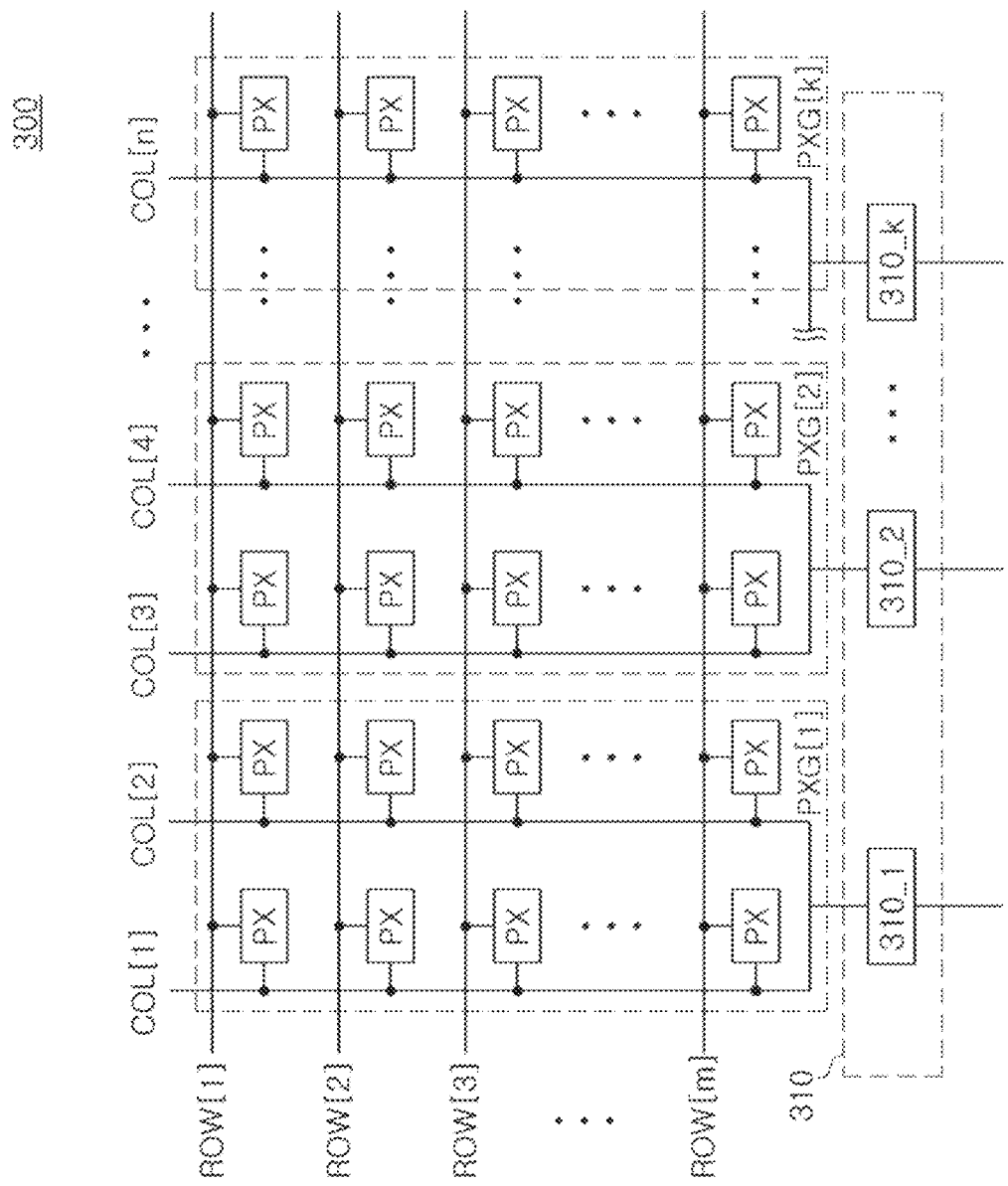

FIGS. 4A and 4B illustrate examples of the pixel array 100 of FIG. 3, according to various embodiments.

Referring to FIGS. 4A and 4B, pixel arrays 200 and 300 may include a plurality of unit pixels PX and leakage current detectors 210 and 310, respectively.

The plurality of unit pixels PX may be arranged in an array form, and may be connected to a plurality of row lines ROW[1] to ROW[m] and a plurality of column lines COL[1] to COL[n]. In an embodiment, the plurality of unit pixels PX may include pixels that respond only to an optical signal having a specific wavelength suitable for obtaining a vital sign. For example, the plurality of unit pixels PX may include pixels that respond only to near-infrared rays reflected by a skin tissue or a blood vessel.

The plurality of unit pixels PX may be grouped into at least one pixel group by an analog binning technique.

In an embodiment, the plurality of unit pixels PX may be grouped in the column lines in a manner that shares an output node of the pixel signal. For example, in an embodiment as illustrated in FIG. 4A, a plurality of unit pixels PX included in the pixel array 200 may constitute different pixel groups PXG[1] to PXG[n] for each column line COL[1] to COL[n], respectively. For example, a plurality of unit pixels PX connected to a first column line COL[1] may constitute a first pixel group PXG[1], and a plurality of unit pixels PX connected to a second column line COL[2] may constitute a second pixel group PXG[2], etc. Similarly, a plurality of unit pixels PX connected to an $n^{th}$ column line COL[n] may constitute an $n^{th}$ pixel group PXG[n]. In another embodiment as illustrated in FIG. 4B, a plurality of unit pixels PX included in the pixel array 300 may constitute different pixel groups PXG[1] to PXG[k] for two column lines COL[1] and COL[2], COL[3] and COL[4], or the like. For example, the plurality of unit pixels PX connected to the first column line COL[1] and the second column line COL[2] constitute the first pixel group PXG[1], and the plurality of unit pixels PX connected to the third column line COL[3] and the fourth column line COL[4] may constitute the second pixel group PXG[2]. Similarly, the plurality of unit pixels PX connected to the n-$1^{th}$ column line COL[n-1] and the $n^{th}$ column line COL[n] may constitute a $k^{th}$ pixel group PXG[k].

In another embodiment, the plurality of unit pixels PX included in the pixel arrays 200 and 300 may be grouped in a row line unit in a manner that shares an output control signal of the pixel signal. For example, the plurality of unit pixels PX connected to the first row line ROW[1] and the second row line ROW[2] may output a pixel signal according to a synchronized selected control signal SEL to constitute a single pixel group.

According to various embodiments, at least one pixel group included in the pixel arrays 200 and 300 may have various shapes and sizes, and the plurality of pixel groups illustrated in FIGS. 4A and 4B may be illustrative. For example, in some embodiments, all of the unit pixels PX included in the pixel arrays 200 and 300 may be grouped to constitute a single pixel group.

The leakage current detectors 210 and 310 may be connected to output nodes of each of the at least one pixel group, and may detect whether leakage currents equal to or greater than a threshold value occur in the plurality of unit pixels PX. The threshold value may be predetermined. For example, in the embodiment as illustrated in FIG. 4A, the leakage current detector 210 may have first to $n^{th}$ leakage current detectors 210_1 to 210_n connected to output nodes of the first to $n^{th}$ pixel groups PXG[1] to PXG[n], respectively. The first to $n^{th}$ leakage current detectors 210_1 to 210_n may detect whether leakage current equal to or greater than the threshold value occurs in the plurality of unit pixels PX included in the first to $n^{th}$ pixel groups PXG[1] to PXG[n], respectively. For example, the first leakage current detector 210_1 may detect whether leakage current equal to or greater than the threshold value occurs in the plurality of unit pixels PX included in the first pixel group PXG[1], and the second leakage current detector 210_2 may detect whether leakage current equal to or greater than the threshold value occurs in the plurality of unit pixels PX included in the second pixel group PXG[2], etc. In the embodiment as illustrated in FIG. 4B, the leakage current detector 310 may have first to $k^{th}$ leakage current detectors 310_1 to 310_k connected to output nodes of the first to $k^{th}$ pixel groups PXG[1] to PXG[k], respectively. The first to $k^{th}$ leakage current detectors 310_1 to 310_k may detect whether leakage current equal to or greater than the threshold value occurs in the plurality of unit pixels PX included in the first to $k^{th}$ pixel groups PXG[1] to PXG[k], respectively. Here, k may be less than n, the number of column lines. For example, the first leakage current detector 310_1 may detect whether leakage current equal to or greater than the threshold value occurs in the plurality of unit pixels PX included in the first pixel group PXG[1] which includes the plurality of unit pixels PX in the first column line COL[1] and the second column line COL[2], and the second leakage current detector 310_2 may detect whether leakage current equal to or greater than the threshold value occurs in the plurality of unit pixels PX included in the second pixel group PXG[2] which includes the plurality of unit pixels PX in the third column line COL[3] and the fourth column line COL[4], etc.

The leakage current detectors 210 and 310 may determine whether a pixel signal received through the output node of each of the at least one pixel group, in a turned-off state of the light source, exceeds the threshold value, and according to a result of the determination, it is possible to control whether or not the pixel signal is output. For example, when a pixel signal received through the output node of the first pixel group PXG[1] is lower than the threshold value, the leakage current detectors 210_1 or 310_1 may output the pixel signal. When a pixel signal received through the output node of the first pixel group PXG[1] is equal to or greater than the threshold value, the leakage current detectors 210_1 or 310_1 may not output the pixel signal.

The sensing module 20 may control whether at least one pixel group is activated in a turned-on state of the light source, based on whether the pixel signal is output from the leakage current detectors 210 and 310 in a turned-off state of the light source. For example, when a pixel signal is output from the leakage current detectors 210 and 310 in a turned-off state of the light source, the sensing module 20 may activate a pixel group generating the pixel signal in a turned-on state of the light source. When a pixel signal is not output from the leakage current detectors 210 and 310, the sensing module 20 may deactivate a pixel group generating the pixel signal in a turned-on state of the light source. In an embodiment, the sensing module 20 may control values of a control signal applied to the plurality of unit pixels PX belonging to a predetermined pixel group to deactivate the pixel group. For example, when the sensing module 20 detects a leakage current equal to or greater than the threshold value in the first pixel group PXG[1], the sensing module 20 may apply a selected control signal SEL having a logic low value (or a value of '0') to the plurality of unit pixels PX belonging to the first pixel group PXG[1], to deactivate the first pixel group PXG[1]. When the sensing module 20 detects a leakage current equal to or greater than the threshold value in the first pixel group PXG[1], the sensing module 20 may apply a transfer control signal TG having a logic low value (or a value of '0') to the plurality of unit pixels PX belonging to the first pixel group PXG[1], to deactivate the first pixel group PXG[1].

Referring to FIG. 3 again for convenience of explanation, the row driver 210 may drive the pixel array 100 in the row line unit. For example, the row driver 210 may generate a transfer control signal for controlling a transfer transistor of the unit pixel PX, a reset control signal for controlling a reset transistor, a selected control signal for controlling a select transistor, or the like, in the row line unit.

The readout circuit 230 may detect a pixel signal output from the unit pixels PX included in the pixel array 100, and may convert the detected pixel signal into a digital signal.

The control logic 250 may control the overall operation of the sensing module 20. In an embodiment, the control logic 250 may control whether the plurality of unit pixels PX are activated, based on whether a pixel signal is output from at least one pixel group included in the pixel array 100.

Hereinafter, a structure of a unit pixel PX that may be included in a pixel array according to an embodiment will be described in detail with reference to FIGS. 5A and 5B.

Figure 5A:
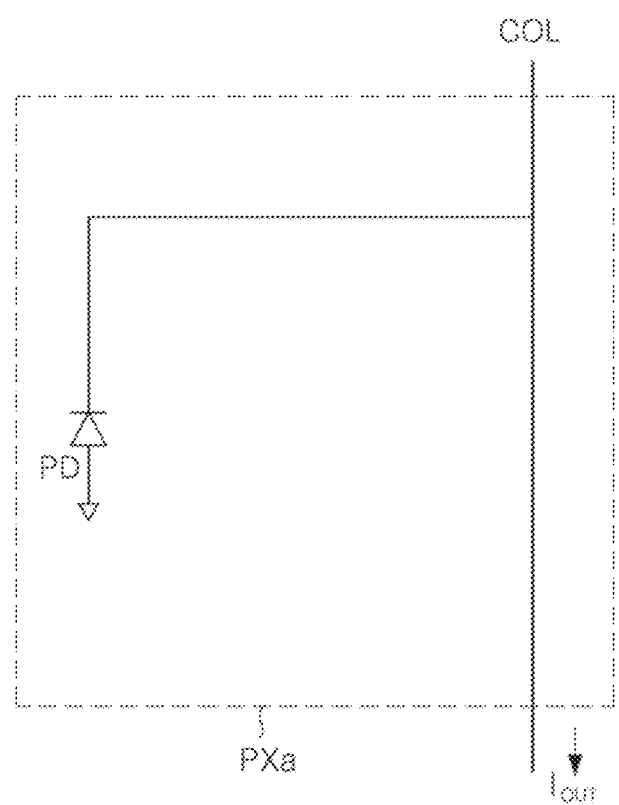
FIGS. 5A and 5B are views illustrating a structure of a unit pixel that may be applied to various embodiments.
Figure 5B:
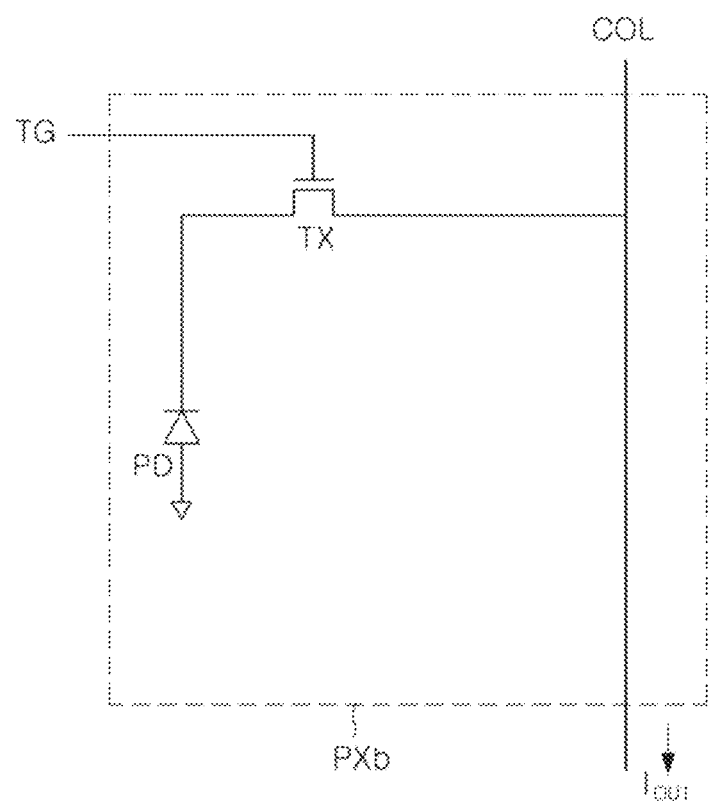

FIGS. 5A and 5B are views illustrating a structure of a unit pixel that may be applied to various embodiments.

Referring to an embodiment illustrated in FIG. 5A, a unit pixel PXa may include at least one photodiode PD connected to a column line COL. When an optical signal output from a light source is reflected from an object and incident on the unit pixel PXa, the photodiode PD may generate electric charge in response to the incident optical signal.

The electric charge generated by the photodiode PD may be transferred through the column line COL and may output as a pixel signal $I_{OUT}$. In this case, the pixel signal $I_{OUT}$ may be a current signal.

Referring to an embodiment illustrated in FIG. 5B, a unit pixel PXb may include at least one photodiode PD and a transfer transistor TX.

The transfer transistor TX may be connected to an output node of the photodiode PD to control transfer of electric charge generated by the photodiode PD to a column line COL. The transfer transistor TX may perform a switching operation according to a transfer control signal TG input through a gate.

A sensing module including the unit pixel PXb may control the switching operation of the transfer transistor TX by using the transfer control signal TG to adjust sensing time.

The electric charge generated by the photodiode PD may be transferred through the column line COL and may output as a pixel signal $I_{OUT}$. In this case, the pixel signal $I_{OUT}$ may be a current signal.

Since the unit pixels PXa and PXb of FIGS. 5A and 5B transfer the electric charge generated by the photodiode PD to the column line COL, amplitudes of pixel signals $I_{OUT}$ may be relatively weak compared to amplitudes of unit pixels of other structures. Therefore, in some embodiments, the number of photodiodes PD included in each of the unit pixels PXa and PXb may be increased to increase amplitudes of the pixel signals $I_{OUT}$. In some embodiments, an amplification ratio of the pixel signal $I_{OUT}$ may be further increased to increase the amplitudes of the pixel signals $I_{OUT}$ compared to cases in which the unit pixels of other structures are applied.

Figure 6:
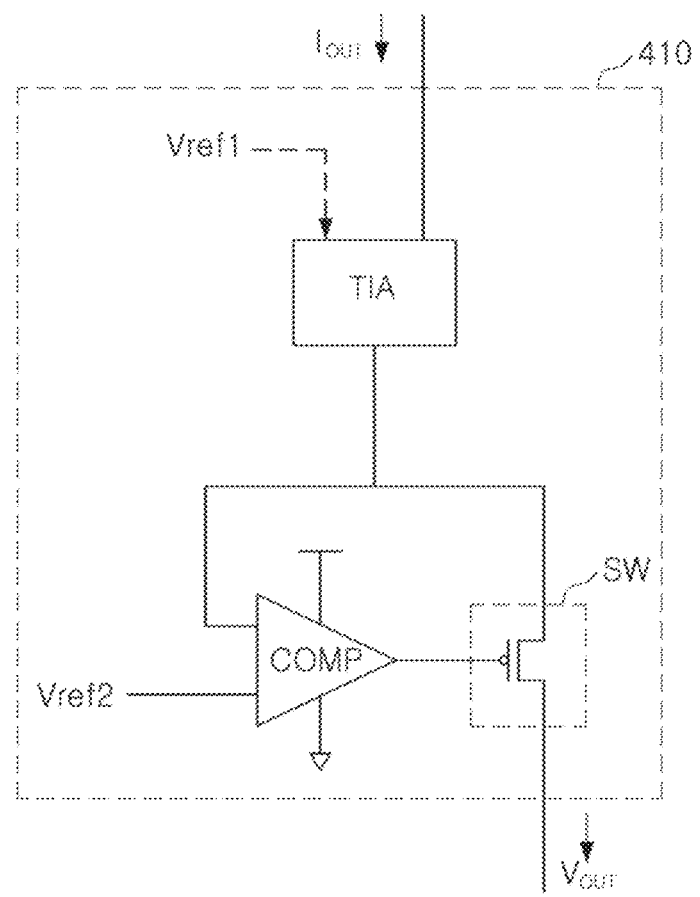
FIG. 6 is a view illustrating a leakage current detector according to an embodiment.

FIG. 6 illustrates an example of a leakage current detector that may be applied to the pixel array including the unit pixels PXa and PXb of FIGS. 5A and 5B.

Referring to FIG. 6, a leakage current detector 410 may include a current-voltage converter TIA, a comparator COMP, and a switch SW.

The current-voltage converter TIA may convert a pixel signal $I_{OUT}$ received through an output node of a pixel group into a voltage signal $V_{OUT}$. In an embodiment, the current-voltage converter TIA may include a transimpedance amplifier that receives a pixel signal $I_{OUT}$ and converts the received pixel signal $I_{OUT}$ into a voltage signal $V_{OUT}$. In an embodiment, the current-voltage converter TIA may include a charge amplifier that receives the pixel signal $I_{OUT}$ and a first reference voltage Vref1, respectively, and converts the received pixel signal $I_{OUT}$ into a voltage signal $V_{OUT}$. The first reference voltage Vref1 may be predetermined. In an embodiment, an amplitude of the first reference voltage Vref1 may be preset to an appropriate value to minimize power consumption of a sensing module. For example, an amplitude of the first reference voltage Vref1 may be 0.1 V or more and 0.5 V or less.

The comparator COMP may compare the voltage signal $V_{OUT}$ with a second reference voltage Vref2, and may output a comparison signal corresponding to a comparison result therefrom. For example, when the pixel signal $V_{OUT}$ is equal to or greater than the second reference voltage Vref2, the comparator COMP may output a comparison signal having a logic high value (or '1' value). When the pixel signal $V_{OUT}$ is less than the second reference voltage Vref2, the comparator COMP may output a comparison signal having a logic low value (or "0" value). The second reference voltage Vref2 may be predetermined. In an embodiment, an amplitude of the second reference voltage Vref2 may vary depending on sensitivity to leakage current, which may be preset according to requirements for a system, or the like. For example, when the sensitivity to leakage current is set to be relatively high, the amplitude of the second reference voltage Vref2 may be less than twice the amplitude of the first reference voltage Vref1 described above. When the sensitivity to leakage current is set to be relatively low, the amplitude of the second reference voltage Vref2 may be equal to or greater than twice the amplitude of the first reference voltage Vref1 described above.

The switch SW may perform a switching operation under control of the comparator COMP, to control whether the voltage signal $V_{OUT}$ is output. For example, when the comparison signal output from the comparator COMP has a logic low value, the switch SW may be turned on such that the leakage current detector 410 outputs the voltage signal $V_{OUT}$. In this case, it may be regarded that a leakage current equal to or greater than a threshold value has occurred in the pixel group generating the voltage signal $V_{OUT}$.

When the comparison signal output from the comparator COMP has a logic high value, the switch SW may be turned off such that the leakage current detector 410 does not output the voltage signal $V_{OUT}$. In this case, it may be considered that a leakage current lower than a threshold value has occurred in the pixel group generating the pixel signal $V_{OUT}$.

In an embodiment, the switch SW may include a transistor having a gate that receives a comparison signal output from the comparator COMP.

A sensing module including the leakage current detector 410 may control whether the pixel group generating a voltage signal $V_{OUT}$ is activated in a turned-on state of the light source, based on whether the voltage signal $V_{OUT}$ is output from the leakage current detector 410. For example, when the leakage current detector 410 outputs the voltage signal $V_{OUT}$, the sensing module may activate the pixel group generating the voltage signal $V_{OUT}$ in a turned-on state of the light source. When the leakage current detector 410 does not output the voltage signal $V_{OUT}$, the sensing module may deactivate the pixel group generating the voltage signal $V_{OUT}$ in a turned-on state of the light source.

In an embodiment, the sensing module may skip a pixel signal detection operation for the pixel group, in a turned-on state of the light source, to deactivate the pixel group. When the unit pixel PXb of FIG. 5B is applied, the sensing module may apply a control signal having a predetermined value, for example, a transfer control signal TG having a logic low value, to the plurality of unit pixels PXb included in the pixel group, to deactivate the pixel group.

Hereinafter, another structure of the unit pixel PX that may be included in the pixel array according to various embodiments will be described in detail with reference to FIGS. 7A and 7B.

Figure 7A:
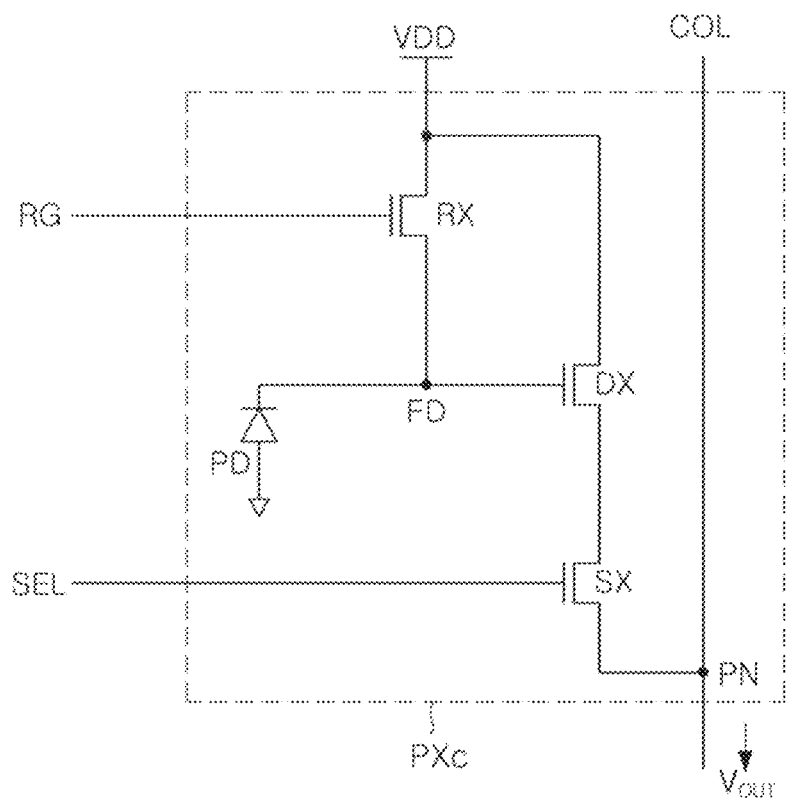
FIGS. 7A and 7B are views illustrating a structure of a unit pixel that may be applied to various embodiments.
Figure 7B:
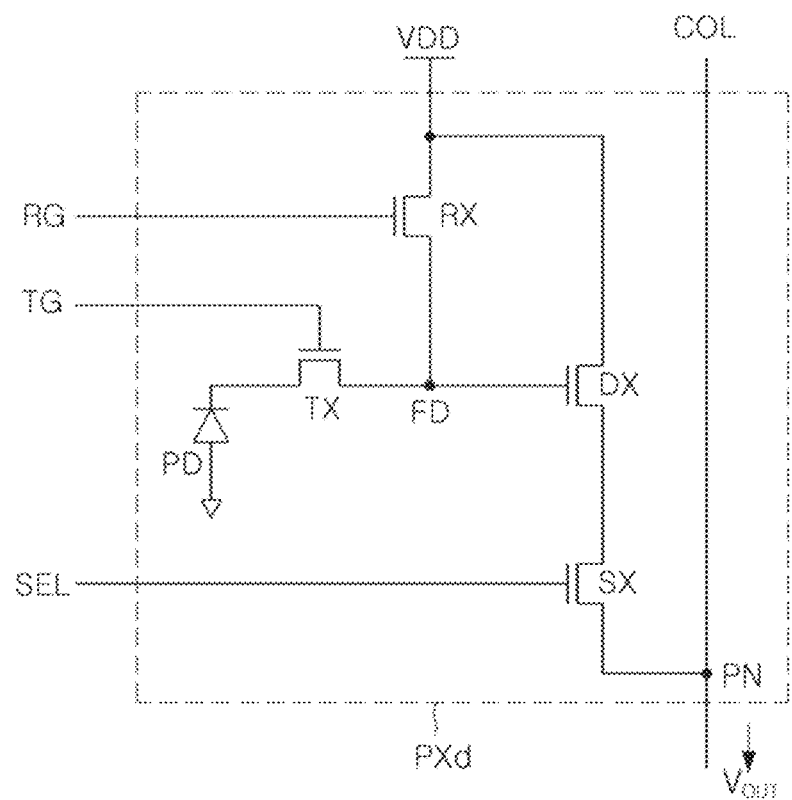

FIGS. 7A and 7B are views illustrating a structure of a unit pixel that may be applied to various embodiments. FIG. 7A illustrates an example of a unit pixel PXc having a 3T structure, and FIG. 7B illustrates an example of a unit pixel PXd having a 4T structure.

Referring to FIG. 7A, the unit pixel PXc may include at least one photodiode PD and a pixel circuit. The pixel circuit may include a floating diffusion FD, a reset transistor RX, a drive transistor DX, and a select transistor SX.

When an optical signal output from a light source is reflected from an object and incident on the unit pixel PXc, the photodiode PD may generate electric charge in response to the incident optical signal. The electric charge generated by the photodiode PD may accumulate in the floating diffusion FD.

When the reset transistor RX is turned on by a reset control signal RG, a voltage of the floating diffusion FD may be reset as a power supply voltage VDD.

After the voltage of the floating diffusion FD is reset, when a transfer transistor TX is turned on by a transfer control signal TG, the electric charge generated by the photodiode PD may move to the floating diffusion FD.

The drive transistor DX may operate as a source-follower amplifier that amplifies a voltage of the floating diffusion FD. When the select transistor SX is turned on by the selected control signal SEL, a voltage signal $V_{OUT}$, which may be a voltage signal corresponding to an amount of the electric charge generated by the photodiode PD, may output to a column line COL through a pixel node PN.

Referring to FIG. 7B, the unit pixel PXd may include at least one photodiode PD and a pixel circuit. The pixel circuit may include a floating diffusion FD, a reset transistor RX, a drive transistor DX, and a select transistor SX. In a different manner to the case of FIG. 7A, the pixel circuit may further include a transfer transistor TX.

The transfer transistor TX may perform a switching operation according to a transfer control signal TG to control transfer of electric charge generated in the photodiode PD to the floating diffusion FD. For example, when the transfer transistor TX is turned on by the transfer control signal TG, the electric charge generated by the photodiode PD may move to the floating diffusion FD. When the transfer transistor TX is turned off by the transfer control signal TG, the electric charge generated by the photodiode PD may not move to the floating diffusion FD.

Figure 8:
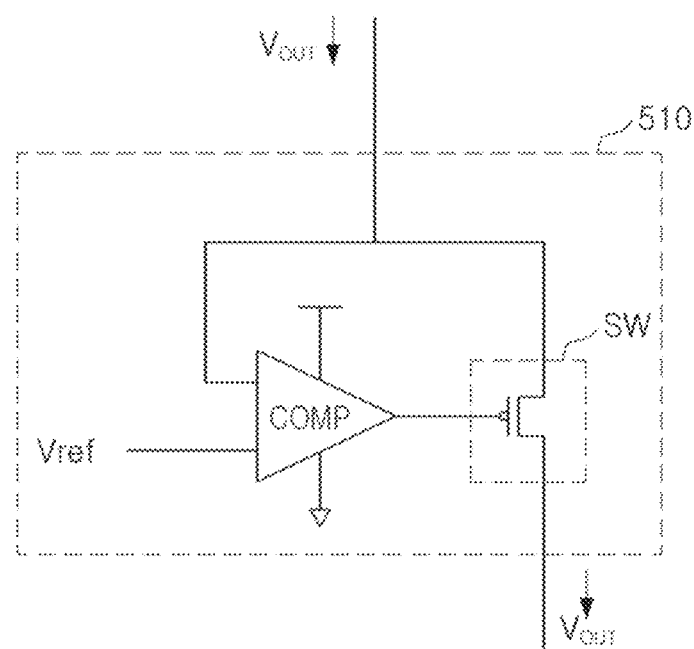
FIG. 8 is a view illustrating a leakage current detector according to an embodiment.

FIG. 8 illustrates an example of a leakage current detector that may be applied to the pixel array including the unit pixels PXc and PXd of FIGS. 7A and 7B, according to an embodiment.

Referring to FIG. 8, a leakage current detector 510 may include a comparator COMP and a switch SW.

The comparator COMP may compare a voltage signal $V_{OUT}$ received through an output node of a pixel group with a reference voltage Vref, and may output a comparison signal corresponding to a comparison result therefrom. For example, when the voltage signal $V_{OUT}$ is equal to or greater than the reference voltage Vref, the comparator COMP may output a comparison signal having a logic high value (or '1' value). When the voltage signal $V_{OUT}$ is less than the reference voltage Vref, the comparator COMP may output a comparison signal having a logic low value (or '0' value). The reference voltage Vref may be predetermined. In an embodiment, an amplitude of the reference voltage Vref may vary depending on sensitivity to leakage current, which may be preset according to requirements for a system. For example, when the sensitivity to leakage current is set to be relatively high, the amplitude of the reference voltage Vref may be less than 1.0V. When the sensitivity to leakage current is set to be relatively low, the amplitude of the reference voltage Vref may be 1.0 V or more.

Hereinafter, an operation method of a sensing module according to an embodiment will be described in detail with reference to FIGS. 9 to 12B.

Figure 9:
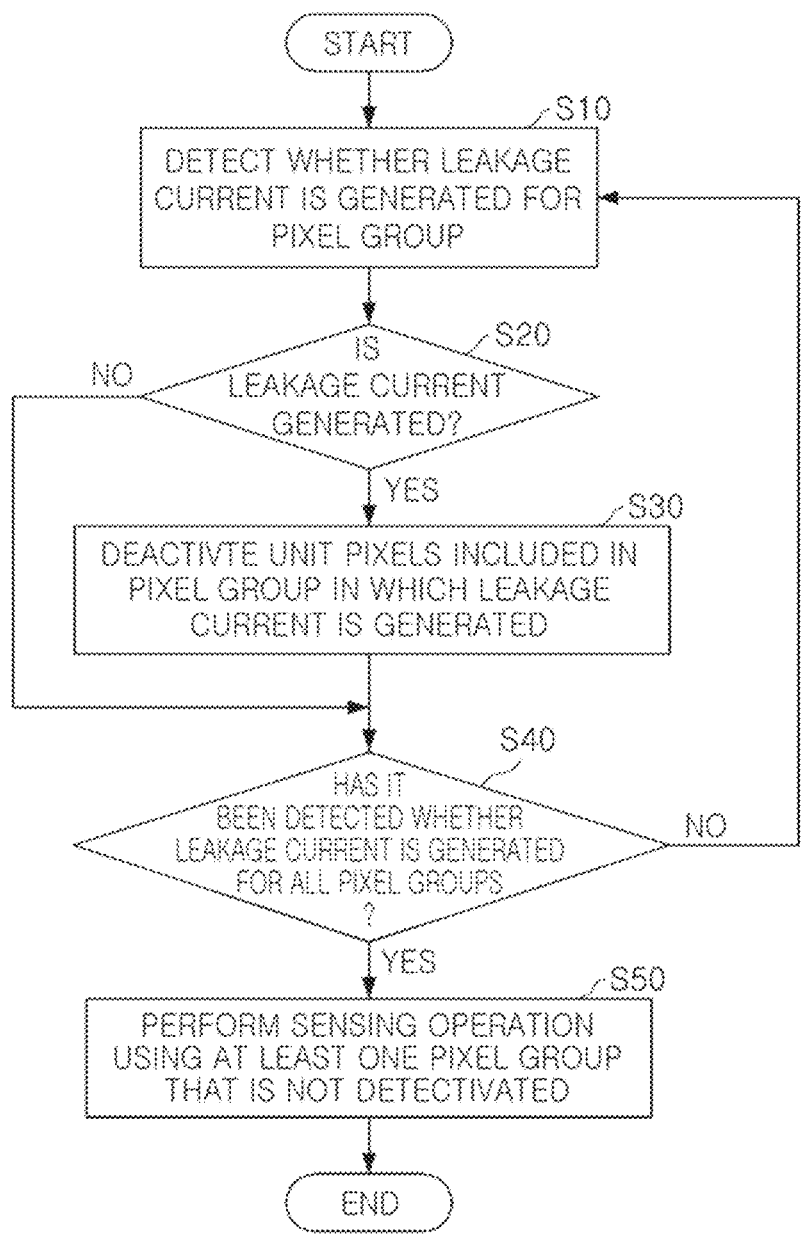
FIG. 9 is a flowchart illustrating a method of operating a sensing module according to an embodiment.

FIG. 9 is a flowchart illustrating a method of operating a sensing module according to an embodiment.

Referring to FIG. 9, a sensing module according to an embodiment may detect a unit pixel in which a leakage current equal to or greater than a threshold value is generated, for a pixel group.

In S10, a leakage current detector may detect whether a leakage current is generated for a pixel group. For example, in a turned-off state of a light source, a leakage current detector connected to an output node of each pixel group may compare a pixel signal generated by each pixel group with a reference voltage, and may output a comparison signal corresponding to a comparison result therefrom. The reference voltage may be predetermined. The leakage current detector may control whether the pixel signal is output in a turned-on state of the light source, based on the comparison signal in a turned-off state of a light source. The sensing module may detect whether the leakage current is generated for each pixel group, according to whether the pixel signal is output from the leakage current detector.

In S20, it is determined whether the leakage current is generated. When the pixel signal is output from the leakage current detector, it may be considered that a leakage current equal to or greater than a threshold value has occurred in the pixel group generating the pixel signal (S20, YES), and, then, the method may proceed to S30.

On the other hand, when the pixel signal is not output from the leakage current detector, it may be considered that no leakage current equal to or greater than the threshold value has occurred in the pixel group (S20, NO), and, then, the method may proceed to S40.

In S30, the sensing module may deactivate a plurality of unit pixels included in the pixel group in which a leakage current is generated. In an embodiment, the sensing module may skip a pixel signal detection operation in a turned-on state of the light source for the pixel group in which a leakage current is generated, to deactivate the pixel group. In another embodiment, the sensing module may apply a control signal having a value, for example, a transfer control signal TG having a logic low value to the plurality of unit pixels included in the pixel group, to deactivate the pixel group. The value may be predetermined.

In S40, the sensing module may determine whether it has been detected whether a leakage current is generated for all pixel groups.

When it has not been determined whether a leakage current is generated for all pixel groups (S40, NO), the method may return to S10 to continuously determine whether a leakage current is generated for any remaining pixel groups.

On the other hand, when it has been determined whether a leakage current is generated for all pixel groups (S40, YES), the sensing module may perform, in a turned-on state of the light source, a sensing operation using at least one pixel group that is not deactivated (S50).

Figure 10B:
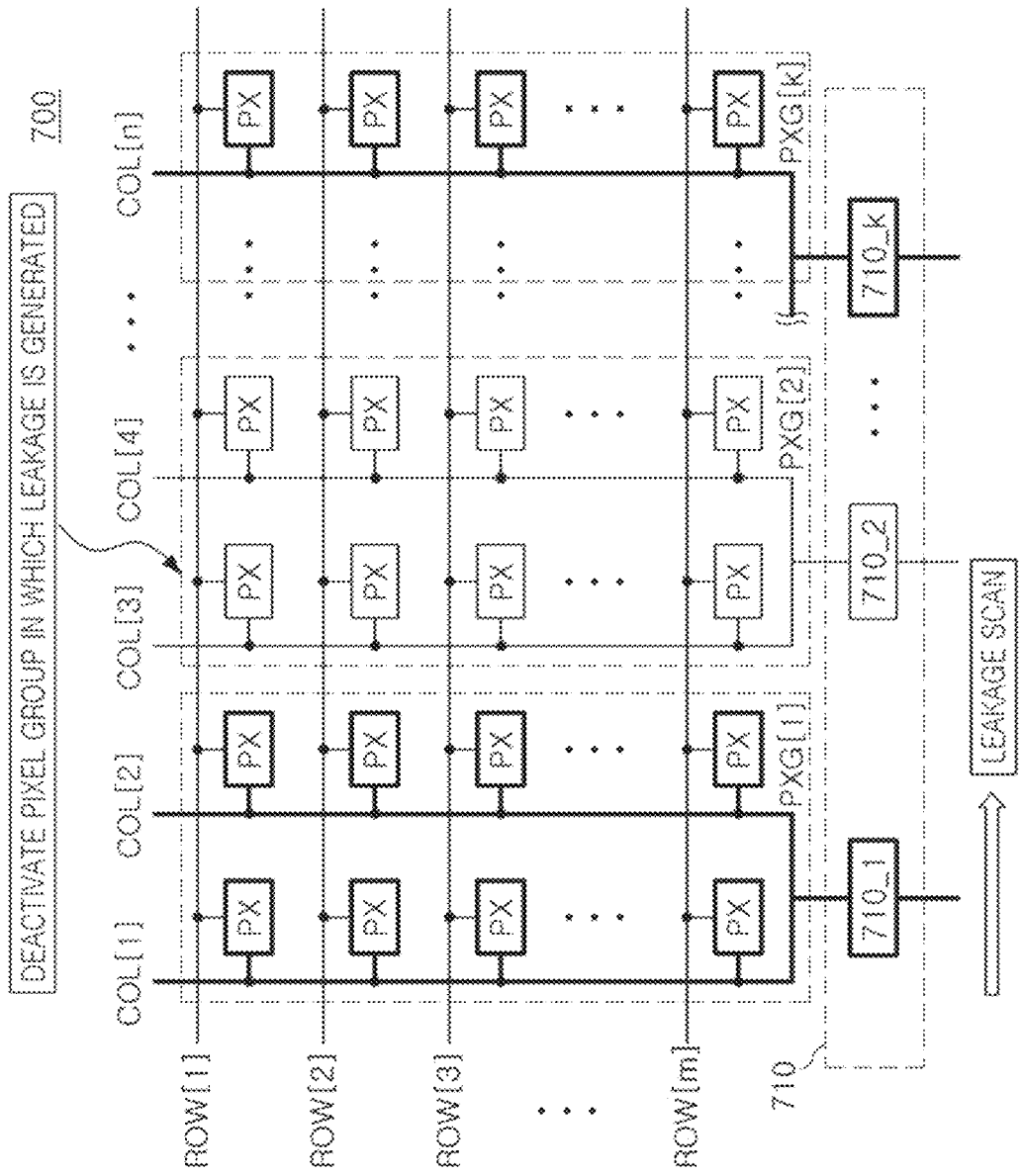

FIGS. 10A and 10B are views illustrating an operation of a sensing module according to the method of FIG. 9, according to an embodiment.

Referring to FIG. 10A, a pixel array 600 according to an embodiment may include a plurality of pixel groups PXG[1] to PXG[n] for column lines COL[1] to COL[n], respectively. The pixel array 600 may be similar to the pixel array 200 illustrated in FIG. 4A.

In a turned-off state of a light source, a leakage current detector 610 of a sensing module may scan whether a leakage current equal to or greater than a threshold value has occurred for the plurality of pixel groups PXG[1] to PXG[n]. The threshold value may be predetermined.

When a pixel group having a leakage current equal to or greater than the threshold value is detected, as a scanned result therefrom, the sensing module may deactivate the pixel group in a turned-on state of the light source. For example, a pixel group PXG[2] from among the pixel groups PXG[1] to PXG[n] may have a leakage current equal to or greater than the threshold value, and the sensing module may deactivate the pixel group PXG[2] in a turned-on state of the light source, as shown in FIG. 10A.

In an embodiment, the sensing module may skip the pixel signal detection operation for the pixel group in a turned-on state of the light source, to deactivate the pixel group. In another embodiment, the sensing module may apply a control signal having a predetermined value, for example, a transfer control signal TG or a selected control signal SEL having a predetermined value, to the plurality of unit pixels included in the pixel group, to deactivate the pixel group.

Referring to FIG. 10B, a pixel array 700 according to an embodiment may include a plurality of pixel groups PXG[1] to PXG[k] for two column lines, for example, COL[1] and COL[2], COL[3] and COL[4], or the like, respectively. The pixel array 700 may be similar to the pixel array 300 illustrated in FIG. 4B.

In a turned-off state of a light source, a leakage current detector 710 of a sensing module may scan whether a leakage current equal to or greater than a threshold value has occurred for the plurality of pixel groups PXG[1] to PXG[k]. The threshold may be predetermined.

When a pixel group having the leakage current equal to or greater than the threshold value is detected, as a scanned result therefrom, the sensing module may deactivate the pixel group in a turned-on state of the light source. In the case of FIG. 10B, since the number of unit pixels PX included in each of the pixel group PXG[1] to PXG[k] may be twice as large as that of FIG. 10A, it may be confirmed that the number of the deactivated unit pixels PX increases under the same condition. For example, when the leakage current occurs in the unit pixel PX disposed at a point at which the second row line ROW[2] and the third column line COL[3] intersect, all of the unit pixels of the pixel group PXG[2] are deactivated, i.e., the unit pixels of COL[3] and COL[4] are deactivated. By contrast, in the case of FIG. 10A under the same condition that the leakage current occurs in the unit pixel PX disposed at the point at which the second row line ROW[2] and the third column line COL[3] intersect, only the unit pixels of COL[3] corresponding to PXG[3] are deactivated. Therefore, the sensing module according to another embodiment may more accurately detect and deactivate a unit pixel in which the leakage current equal to or greater than the threshold value is detected in the pixel unit, to prevent the sensing accuracy from being lowered.

Hereinafter, a sensing module according to another embodiment will be described in more detail with reference to FIGS. 11A to 13.

Figure 11A:
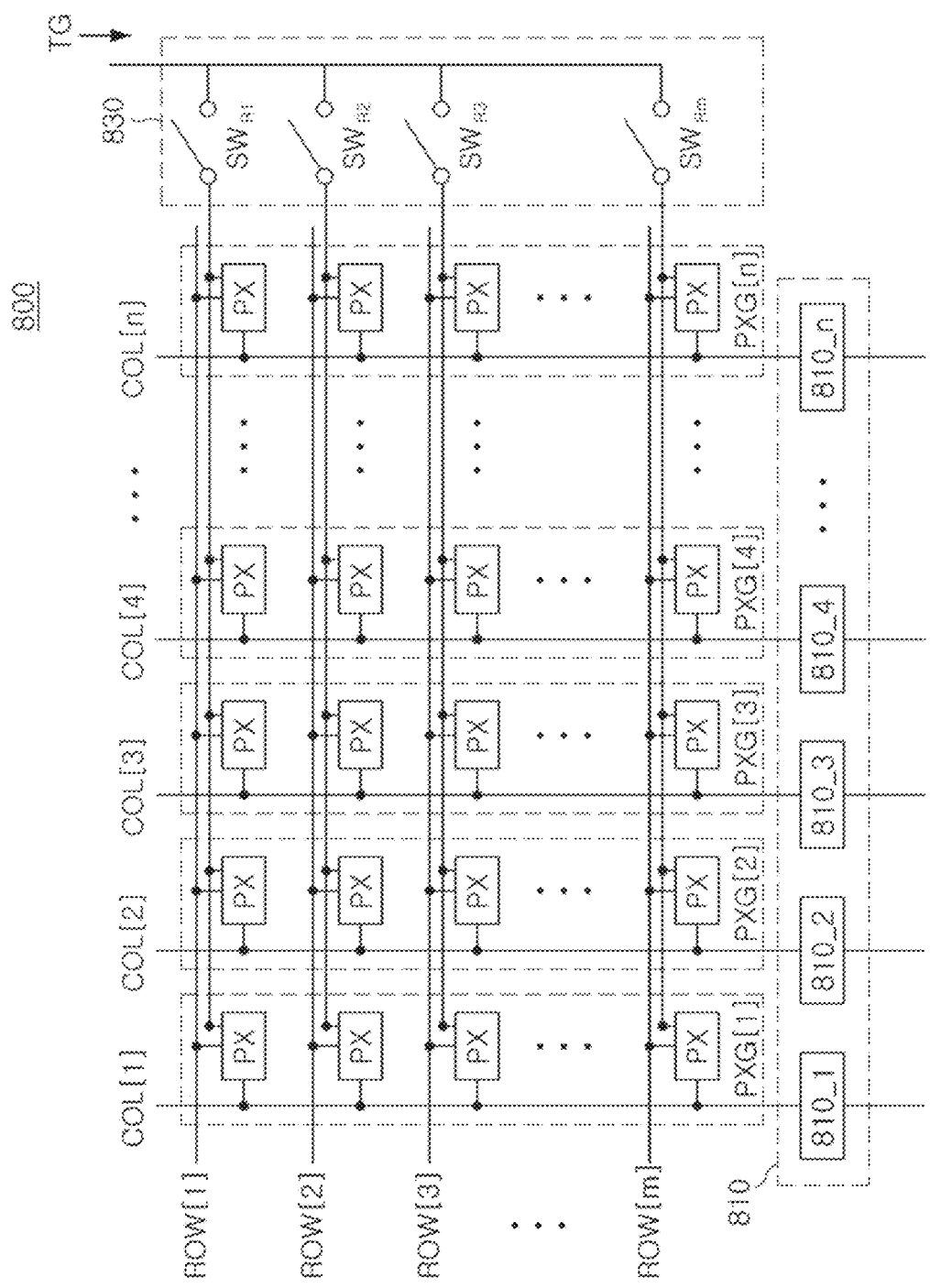
FIGS. 11A and 11B are views illustrating a pixel array according to various embodiments.
Figure 11B:
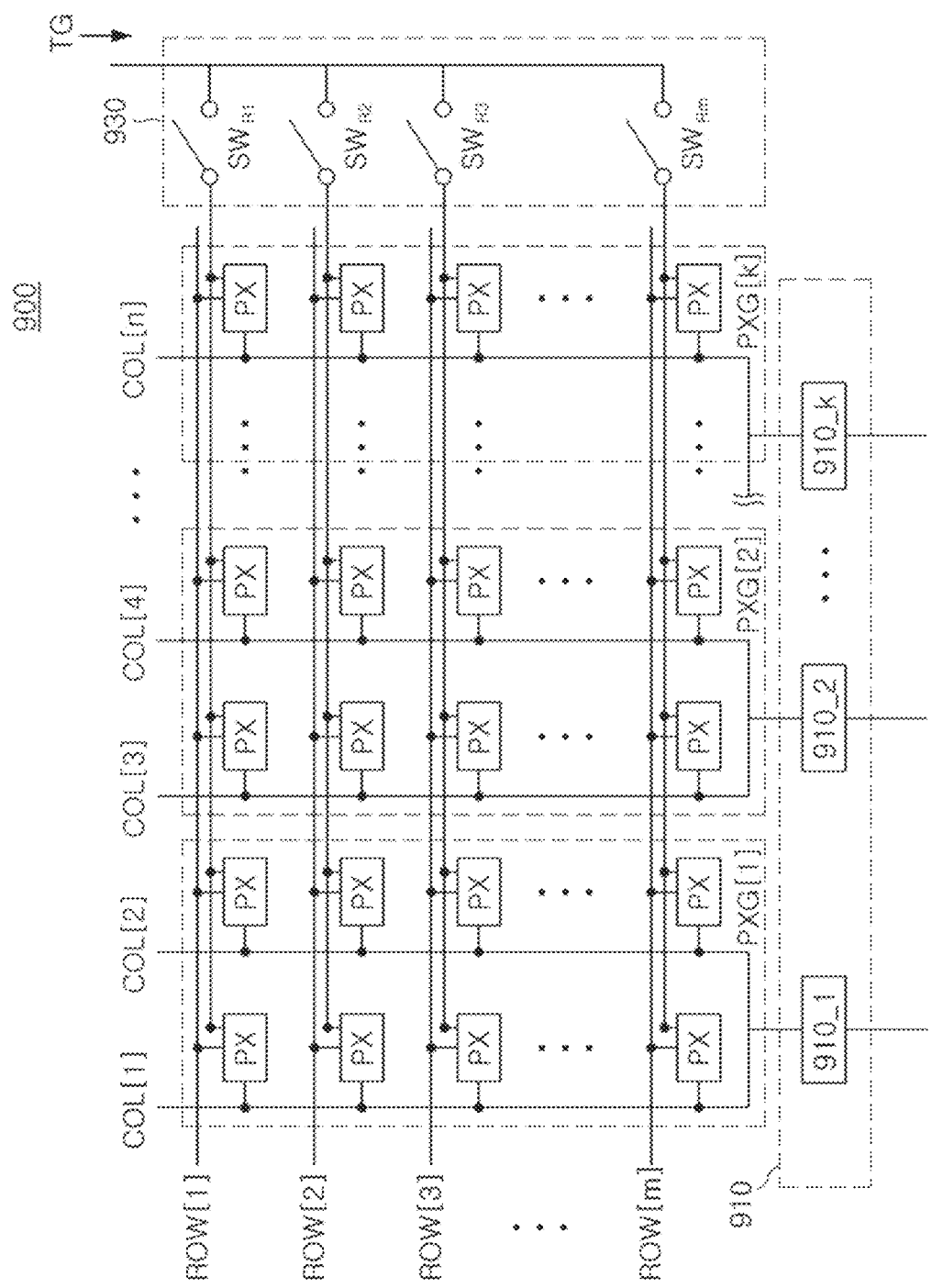

FIGS. 11A and 11B are views illustrating a pixel array according to various embodiments.

Referring to FIGS. 11A and 11B, pixel arrays 800 and 900 may include a plurality of unit pixels PX, first leakage current detectors 810 and 910, and second leakage current detectors 830 and 930, respectively. When the plurality of unit pixels PX are arranged in a matrix form, the unit pixels PX may be arranged at points at which a plurality of row lines ROW[1] to ROW[m] and a plurality of column lines COL[1] to COL[n] intersect.

The plurality of unit pixels PX may be grouped into at least one pixel group by an analog binning technique. For example, in the embodiment illustrated in FIG. 11A, the plurality of unit pixels PX included in the pixel array 800 may constitute different pixel groups PXG[1] to PXG[n] that include unit pixels PX of column line COL[1] to COL[n], respectively. In the embodiment illustrated in FIG. 11B, the plurality of unit pixels PX included in the pixel array 900 may constitute different pixel groups PXG[1] to PXG[k] that each include unit pixels PX of two column lines COL[1] and COL[2], COL[3] and COL[4], or the like. The above may be only an example for convenience of explanation, and embodiments are not limited thereto. For example, all of the unit pixels PX included in the pixel array 800 may be grouped to form a single pixel group.

The first leakage current detectors 810 and 910 may be connected to output nodes of each pixel group, to detect whether a leakage current equal to or greater than a threshold value occurs for the plurality of unit pixels PX in a pixel group. The configuration of the first leakage current detectors 810 and 910 may be as described above with reference to FIGS. 6 and 8.

The second leakage current detectors 830 and 930 may include a plurality of switches $SW_{R1}$ to $SW_{Rm}$ connected to the plurality of row lines ROW[1] to ROW[m], respectively. The second leakage current detectors 830 and 930 may apply a control signal, for example, a transfer control signal TG through a switching operation of the plurality of switches $SW_{R1}$ to $SW_{Rm}$, to each of the plurality of unit pixels PX connected to the plurality of row lines ROW[1] to ROW[m], to activate the plurality of unit pixels PX in a row line. The control signal may be predetermined. In this configuration, the first leakage current detectors 810 and 910 may detect the pixel signals of the plurality of unit pixels activated by the second leakage current detectors 830 and 930, respectively, to detect the unit pixels PX in which the leakage current has occurred. In this configuration, the number of detected unit pixels PX may be proportional to the number of column lines included in a pixel group. For example, in the case of FIG. 11A, the sensing module may actually detect only the unit pixel (e.g., the unit pixel connected to the second row line ROW[2] and the second column line COL[2]) in which a leakage current equal to or greater than a threshold value has occurred. In the case of FIG. 11B, the sensing module may actually detect a unit pixel (e.g., a unit pixel connected to the second row line ROW[2] and the third column line COL[3]) in which a leakage current equal to or greater than a threshold value is generated, and a unit pixel (e.g., a unit pixel connected to the second row line ROW[2] and the fourth column line COL [4]) grouped on the same row line as the unit pixel above described (i.e., the second row line ROW[2]) as a unit pixel in which a leakage current is generated.

The above-described operations may be carried out by specifying a pixel group in which a leakage current is generated by the first leakage current detectors 810 and 910, applying a control signal for each row line by the second leakage current detectors 830 and 930 for the specified pixel group, and then detecting pixel signals generated by the activated unit pixels PX by the first leakage current detectors 810 and 910.

The above-described operations may be also carried out by applying a control signal for each row line by the second leakage current detectors 830 and 930 to activate the plurality of unit pixels PX connected to each of the row lines, and then detecting pixel signals generated by the activated unit pixels PX for each pixel group by the first leakage current detectors 810 and 910.

The structure of the unit pixel PX that may be included in the pixel arrays 800 and 900 may be as described above with reference to FIGS. 5A, 5B, 7A, and 7B.

Figure 12:
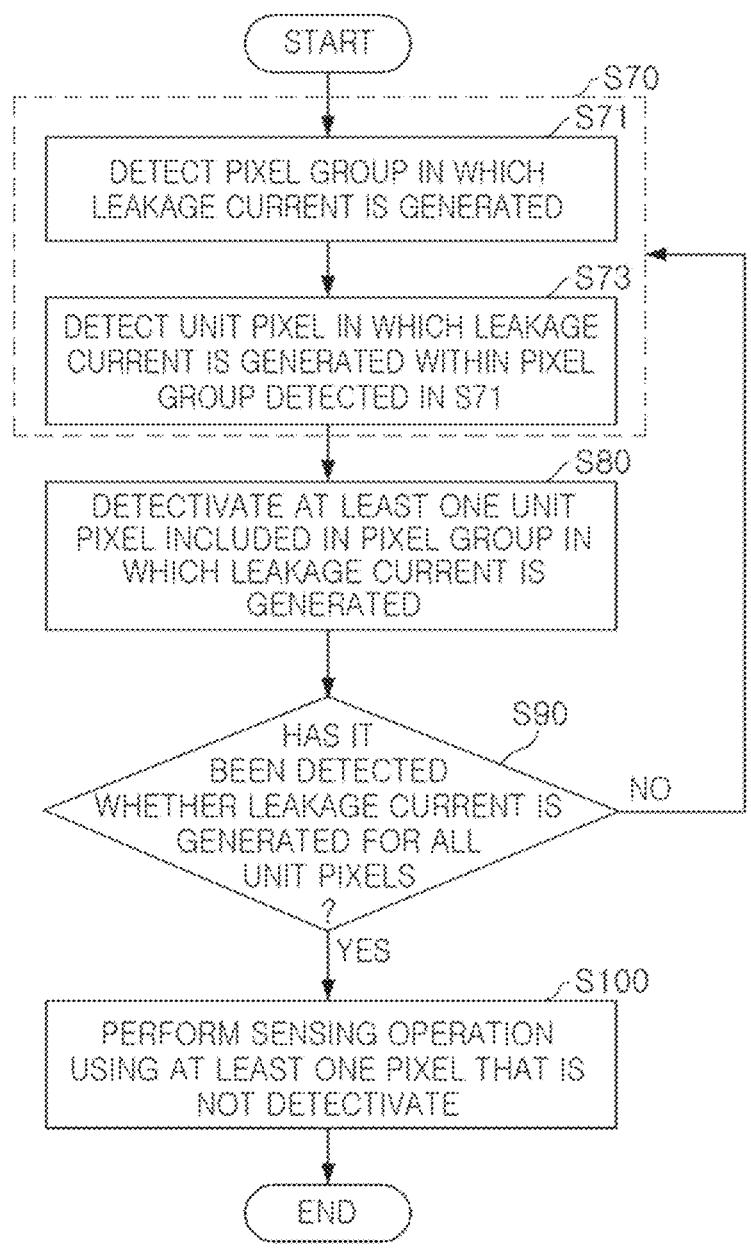
FIG. 12 is a flowchart illustrating a method of operating a sensing module according to an embodiment.
Figure 13:
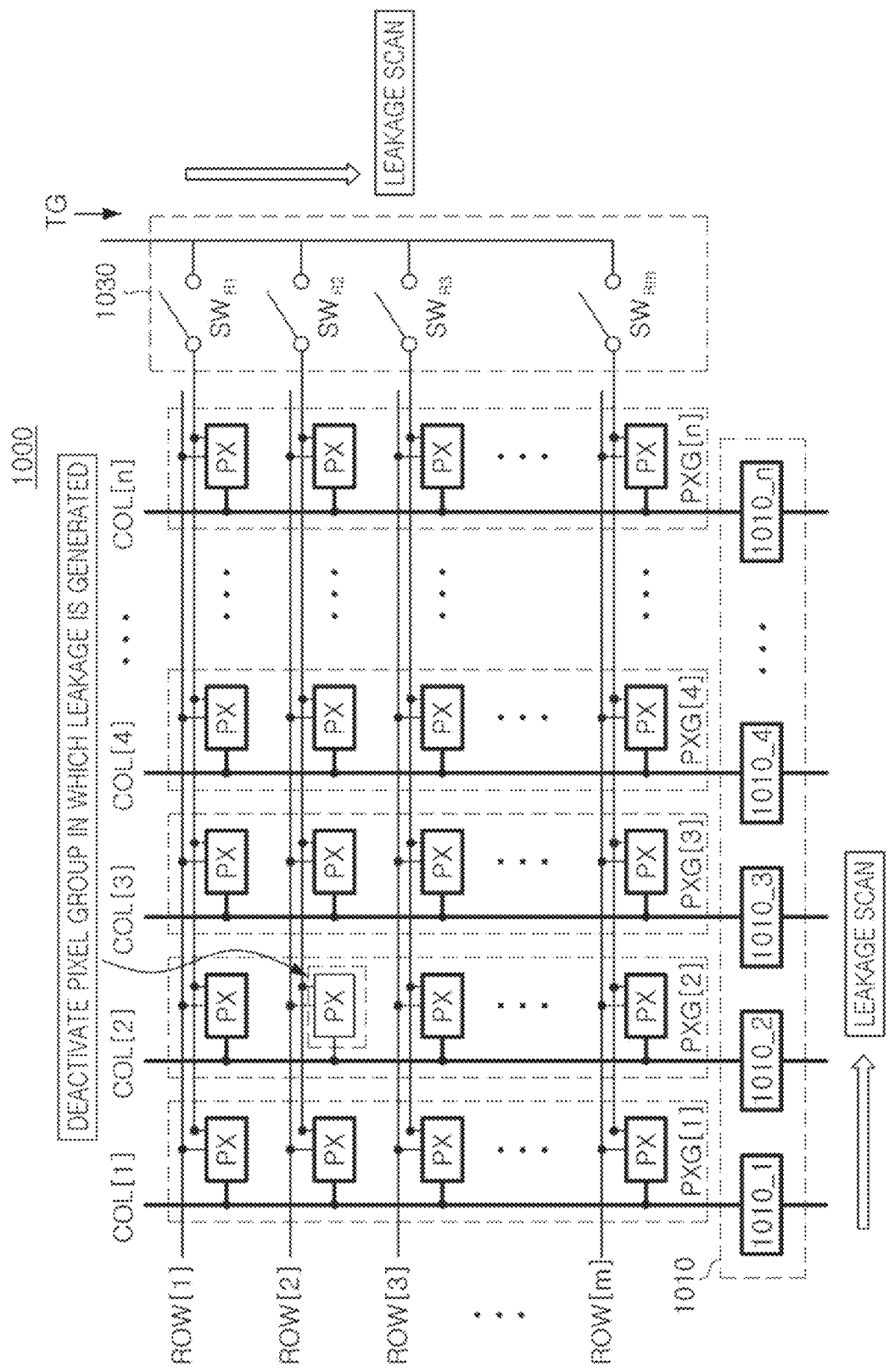
FIG. 13 is a view illustrating an operation of a sensing module according to the method of FIG. 12, according to an embodiment.

Referring to FIGS. 12 and 13, a method of operating a sensing module according to an embodiment will be described in detail.

FIG. 12 is a flowchart illustrating a method of operating a sensing module according to an embodiment.

Referring to FIG. 12, in a different manner to the sensing module described above with reference to FIGS. 9 to 10B, a sensing module according to an embodiment may more accurately detect a unit pixel in which a leakage current equal to or greater than a threshold value is generated. That is, the sensing module may deactivate the unit pixel, in a pixel unit, in which the leakage current occurs in a turned-on state of a light source, to increase the sensing accuracy.

In S70, the sensing module may detect unit pixels in which a leakage current is generated in a predetermined pixel unit. The sensing module may detect a unit pixel group in which a leakage current is generated (S71). For example, the sensing module may detect the unit pixel in which the leakage current is generated by the first leakage current detector for each pixel group. The sensing module may detect a unit pixel in which the leakage current is generated within the pixel group detected in S71 (S73). For example, the sensing module may activate the plurality of unit pixels in a row line unit (i.e., row by row) by the second leakage current detector, to detect a unit pixel in which the leakage current has occurred within the pixel group detected in S71.

In S80, the sensing module may deactivate at least one unit pixel included in pixel group in which leakage current is generated S80. For example, the sensing module may deactivate at least one unit pixel included in the pixel group that has been detected as having the leakage current, in a turned-on state of a light source. In an embodiment, the sensing module may apply a control signal having a value to the unit pixels, for example, a transfer control signal TG or a selected control signal SEL having a logic low value, to deactivate the pixel group. The value may be predetermined.

In S90, the sensing module may determine whether it has been detected whether a leakage current is generated for all of the unit pixels.

When it is determined that it has not been determined whether the leakage current has occurred for all of the unit pixels (S90, NO), the operation may return to S70 to continuously determine whether the leakage current has occurred for remaining unit pixels.

When it is determined that it has been determined whether the leakage current has occurred for all of the unit pixels (S90, YES), the sensing module may perform a sensing operation using at least one unit pixel that is not deactivated, in a turned-on state of the light source (S100).

FIG. 13 is a view illustrating an operation of a sensing module according to the method of FIG. 12, according to an embodiment.

Referring to FIG. 13, a pixel array 1000 according to an embodiment may include a plurality of pixel groups PXG[1] to PXG[n] configured for each column line COL[1] to COL[n].

In a turned-off state of a light source, a first leakage current detector 1010 of a sensing module may scan to detect whether a leakage current equal to or greater than a threshold value has occurred for the plurality of pixel groups PXG[1] to PXG[n]. In the specific example illustrated in FIG. 13, the first leakage current detector 1010 may scan and detect that the pixel group PXG[2] has a leakage current equal to or greater than the threshold value.

When a pixel group having the leakage current equal to or greater than the threshold value is detected, as a scanned result there from, a second leakage current detector 1030 may activate a plurality of unit pixels PX included in the pixel group in a row line unit (i.e., row by row). The first leakage current detector 1010 may compare a pixel signal output from the activated unit pixel PX in the pixel group with a reference voltage, to detect the unit pixels PX within the detected pixel group in which a leakage current equal to or greater than a threshold value is generated. In the specific example illustrated in FIG. 13, the second leakage current detector 1030 may activate the plurality of unit pixels PX included in the pixel group PXG[2], and the first leakage current detector 1010 may detect that the unit pixel PX at the point that ROW[2] intersects with COL[2] in which the leakage current equal to or greater than the threshold value is generated.

The sensing module may deactivate the detected unit pixel PX in a turned-on state of a light source. In the specific example illustrated in FIG. 13, the unit pixel PX at the point that ROW[2] intersects COL[2] may be deactivated in a turned-on state of the light source.

Figure 14A:
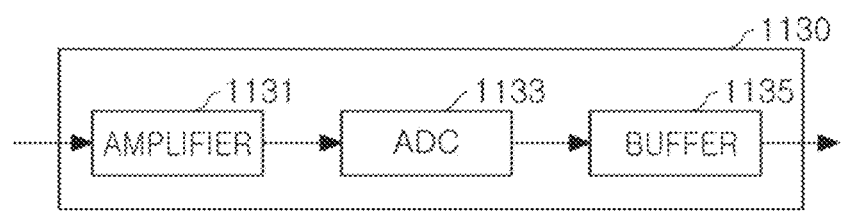
FIGS. 14A and 14B are views illustrating configurations of a readout circuit that may be applied to the sensing module described with reference to FIGS. 1 to 13, according to an embodiment.
Figure 14B:
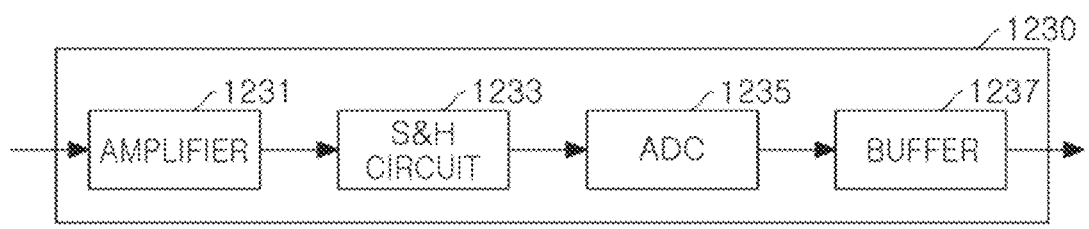

FIGS. 14A and 14B illustrate examples of a readout circuit that may be included in a sensing module, according to various embodiments.

Referring to FIG. 14A, a readout circuit 1130 may include an amplifier 1131, an analog-digital converter (ADC) 1133, and a buffer 1135.

The amplifier 1131 may amplify a pixel signal output from each pixel group at an amplification ratio. The amplification ratio may be predetermined. The analog-digital converter 1133 may convert the pixel signal amplified by the amplifier 1131 into a digital signal. The pixel signal converted into the digital signal may be stored in the buffer 1135.

Referring to FIG. 14B, in a different configuration to that of FIG. 14A, a readout circuit 1230 may include an amplifier 1231, an ADC 1235 and a buffer 1237 similar to FIG. 14A, and may further include a sample and hold (S & H) circuit 1233 between the amplifier 1231 and the ADC 1235. The S & H circuit 1233 may store a pixel signal output from each pixel group. In an embodiment, the S & H circuit 1233 may include a correlated double sampler CDS.

When a sensing module according to an embodiment has a monolithic stacked structure, the readout circuits 1130 and 1230 may further include a digital binning circuit that performs a digital binning operation for a pixel signal converted into a digital signal. In an embodiment, the digital binning circuit may perform a digital binning operation by applying a weight to a plurality of pixel signals stored in the buffers 1135 and 1237, and then performing an accumulated averaging operation for a result therefrom. The weight may be predetermined.

Figure 15:
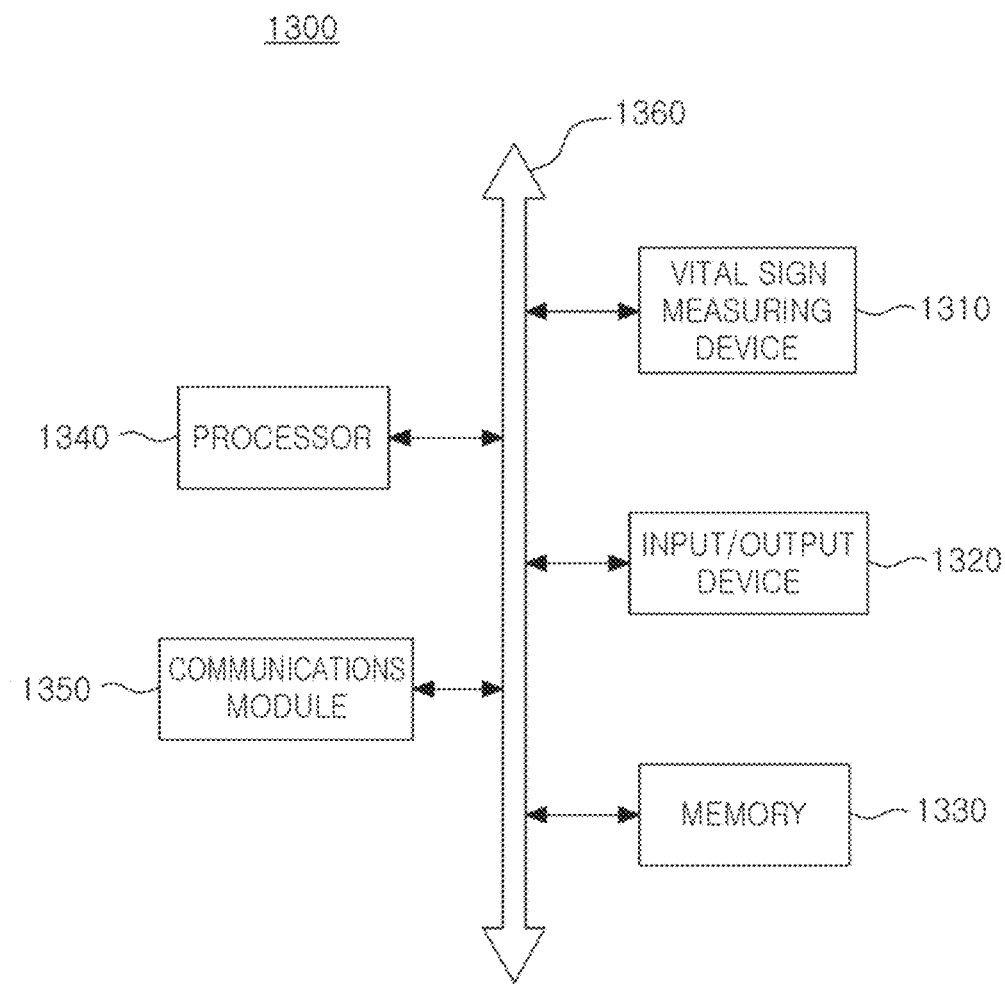
FIG. 15 is a view schematically illustrating a configuration of an electronic device including a vital sign measuring device according to various embodiments.

FIG. 15 is a block diagram schematically illustrating an electronic device including a vital sign measuring device according to various embodiments.

Referring to FIG. 15, an electronic device 1300 may include a vital sign measuring device 1310, an input/output device 1320, a memory 1330, a processor 1340, and a communications module 1350. The electronic device 1300 may be a concept encompassing a smartphone, a tablet PC, a smart wearable device, and the like.

The vital sign measuring device 1310 may be as described above with reference to FIGS. 1 to 14, may be mounted on a package substrate or the like, and may be connected to the processor 1340 through a bus 1360 or other communications means.

The input/output device 1320 may include input devices such as a keyboard, a mouse, and a touch screen provided to a user, and output devices such as a display and an audio output unit.

The memory 1330 may be a storage medium that stores data necessary for an operation of the electronic device 1300 or multimedia data. The memory 1330 may include a volatile memory or a nonvolatile memory such as a flash memory. The memory 1330 may include at least one of a solid state drive (SSD), a hard disk drive (HDD), or an optical drive (ODD) as a storage device.

The processor 1340 may perform specific operations, commands, tasks, and the like. The processor 1340 may be a central processing unit (CPU) or microprocessor unit (MCU), a system on a chip (SoC), or the like, and may be connected via the bus 1360 to the vital sign measuring device 1310, the input/output device 1320, and the memory 1330, as well as to other units connected through the communications module 1350.

Figure 16:
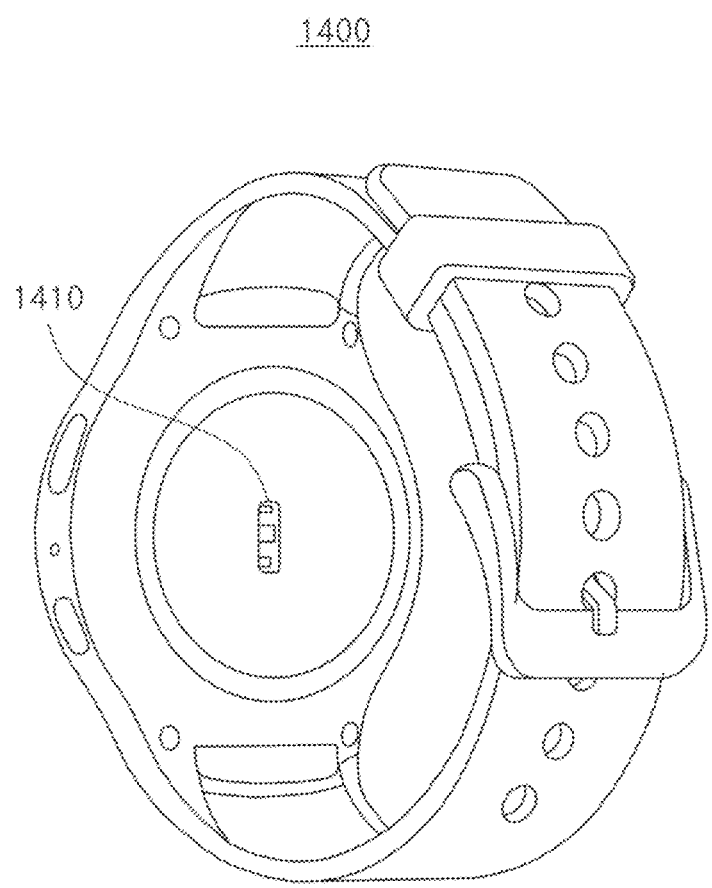
FIGS. 16 to 18 are views illustrating an electronic device including a vital sign measuring device according to various embodiments.
Figure 17:
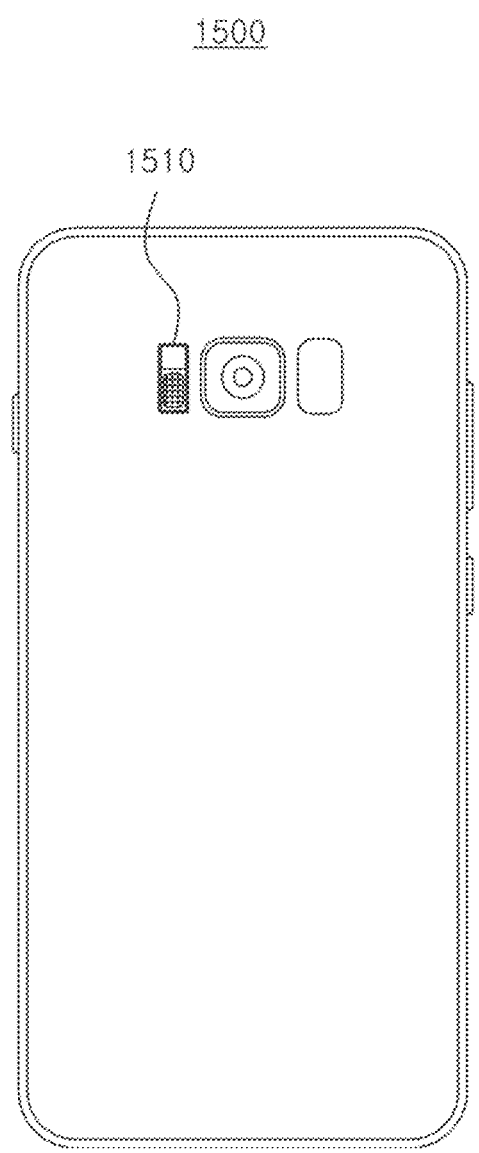
Figure 18:
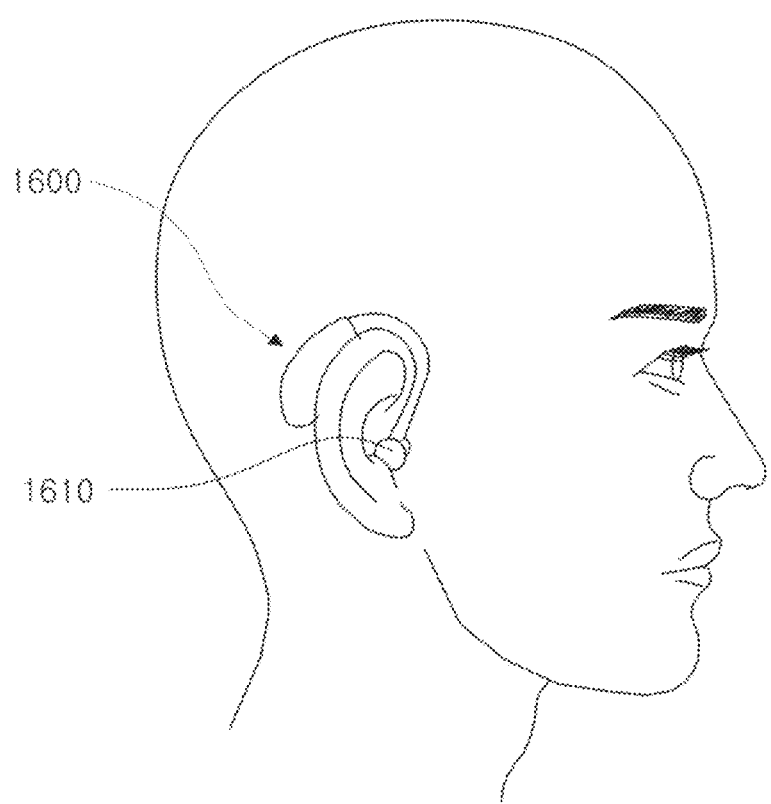

FIGS. 16 to 18 are views illustrating an electronic device including a vital sign measuring device according to various embodiments.

Referring to FIG. 16, an electronic device 1400 may be implemented as a watch type wearable device.

The electronic device 1400 may include a main body and a wrist strap. A display may be provided on a front surface of the main body, to display various application screens including time information, received message information, and the like. A user may wear the electronic device 1400 on his/her wrist using the strap.

A vital sign measuring device 1410 may be disposed on a rear surface of the main body. The vital sign measuring device 1410 may output an optical signal to a body region contacting the rear surface of the main body, such as a user's wrist, or the like, and may sense light reflected therefrom to measure a vital sign. The electronic device 1400 may analyze the vital sign measured by the vital sign measuring device 1410 to obtain vital information of the user such as blood pressure, blood vessel age, arteriosclerosis, aortic pressure waveform, stress index, or the like.

Referring to FIG. 17, an electronic device 1500 may be implemented as a mobile device such as a smartphone.

The electronic device 1500 may include a housing and a display panel.

The housing may form an appearance of the electronic device 1500. The housing may include a first surface, a second surface, opposite to the first surface, and a side surrounding a space between the first surface and the second surface.

A display panel and a cover glass may be sequentially arranged on the first surface of the housing. The display panel may be exposed externally through the cover glass.

A vital sign measuring device 1510, a camera module, an infrared sensor, or the like may be arranged on the second surface of the housing.

When a user requests vital information through an application or the like on the electronic device 1500, the application may request the vital sign measuring device 1510 to measure a vital sign. The vital sign measuring device 1510 may sense reflected light obtained from a portion of the user's body to measure the vital sign. The electronic device 1500, e.g., the application, may analyze the vital sign measured by the vital sign measuring device 1510 to obtain vital information of the user.

Referring to FIG. 18, an electronic device 1600 may also be implemented as an ear wearable device.

The electronic device 1600 may include a main body and an ear strap.

A user may wear the electronic device 1600 by hooking the ear strap to an ear wheel. With the user wearing the electronic device 1600, the main body may be inserted into an external auditory meatus of the user.

The main body may be equipped with a vital sign measuring device 1610. The vital sign measuring device 1610 may output an optical signal to a body region contacting the main body, such as a wall of the external auditory meatus of the user, and may detect light reflected therefrom to measure a vital sign. The wall of the external auditory meatus of the user may be thinner than other areas of the body to facilitate measurement of the vital sign such as blood flow or the like. The electronic device 1600 may analyze the vital sign measured by the vital sign measuring device to obtain vital information of the user.

A sensing module according to various embodiments may minimize power consumption by deactivating a pixel group including a unit pixel in which a leakage current is generated.

A sensing module according to various embodiments may increase sensing accuracy by deactivating a unit pixel in which a leakage current is generated.

Various advantages and effects of the present disclosure are not limited to the above description, and will be more readily understood from the specific embodiments described herein.

While embodiments have been illustrated and described above, it will be apparent to those skilled in the art that modifications and variations may be made without departing from the scope of the present inventive concept as defined by the appended claims.

What is claimed is:

1. A sensing module comprising:
   a light source that outputs an optical signal;
   a plurality of unit pixels that are connected to a plurality of row lines and a plurality of column lines, and that sense the optical signal to generate a pixel signal;

a leakage current detector that compares an amplitude of the pixel signal generated by the plurality of unit pixels with a first reference voltage, in a state in which the light source is deactivated, to detect a unit pixel group, among the plurality of unit pixels, in which a leakage current equal to or greater than a threshold value is generated; and a pixel driving circuit that deactivates the detected unit pixel group in a state in which the light source is activated.

2. The sensing module according to claim 1, wherein the plurality of unit pixels are grouped in a predetermined unit to provide at least one pixel group.

3. The sensing module according to claim 2, wherein the plurality of unit pixels are grouped in the predetermined unit to provide a plurality of pixel groups, and the leakage current detector comprises a plurality of leakage current detectors, each of the plurality of leakage current detectors connected to an output node of a respective one of the plurality of pixel groups.

4. The sensing module according to claim 1, wherein the leakage current detector comprises:

a comparator having a first input that receives the pixel signal and a second input that is connected to the first reference voltage, and an output that outputs a comparison signal corresponding to a comparison result of the pixel signal and the first reference voltage; and a switch that performs a switching operation according to the comparison signal to control whether the pixel signal is output.

5. The sensing module according to claim 4, wherein the switch comprises a transistor having a gate connected to the output of the comparator.

6. The sensing module according to claim 4, wherein the leakage current detector further comprises a current-voltage converter that converts the pixel signal into a voltage signal and outputs the converted voltage signal to the first input of the comparator.

7. The sensing module according to claim 6, wherein the current-voltage converter converts the pixel signal into the voltage signal based on a second reference voltage that is different from the first reference voltage.

8. The sensing module according to claim 1, wherein the pixel driving circuit comprises:

an amplifier that amplifies pixel signals generated by an activated unit pixel group among the plurality of unit pixels; and an analog-digital converter that converts the amplified pixel signals into digital signals.

9. The sensing module according to claim 8, wherein the pixel driving circuit further comprises a binning circuit that adds a weight to the digital signals.

10. A sensing module comprising:

a plurality of unit pixels that are connected to a plurality of row lines and a plurality of column lines, the plurality of unit pixels being grouped in a predetermined unit to form at least one pixel group;

a first leakage current detector that is connected to an output node of the at least one pixel group, respectively, and that compares an amplitude of a pixel signal generated at the output node of the at least one pixel group with a reference voltage, to detect a pixel group in which a leakage current equal to or greater than a threshold value is generated; and a second leakage current detector that activates the plurality of unit pixels row line by row line, wherein the first leakage current detector compares an amplitude of a pixel signal at the output node of the detected pixel group that is generated by each of the plurality of unit pixels activated by the second leakage current detector with the reference voltage, to detect a unit pixel included in the detected pixel group, in which the leakage current has occurred, and wherein the detected unit pixel in which the leakage current has occurred is deactivated in a turned-on state of a light source.

11. The sensing module according to claim 10, wherein the first leakage current detector comprises:

a comparator having a first input that receives the pixel signal and a second input that is connected to a first reference voltage, and an output that outputs a comparison signal corresponding to a comparison result of the pixel signal and the first reference voltage; and a switch that performs a switching operation according to the comparison signal to control whether the pixel signal is output.

12. The sensing module according to claim 11, wherein the first leakage current detector further comprises a current-voltage converter that converts the pixel signal into a voltage signal and outputs the converted voltage signal to the first input of the comparator.

13. The sensing module according to claim 10, wherein the second leakage current detector is configured to apply a synchronized transfer control signal to the plurality of unit pixels connected to each of the plurality of row lines, to activate the plurality of unit pixels row line by row line.

14. The sensing module according to claim 10, wherein the second leakage current detector comprises a plurality of switches that supply a control signal to activate the plurality of unit pixels row line by row line.

15. The sensing module according to claim 10, wherein the sensing module obtains a pixel signal from an activated unit pixel, among the plurality of unit pixels, in the turned-on state of the light source, and digitally converts the obtained pixel signal to generate a sensing signal.

16. The sensing module according to claim 10, wherein the reference voltage varies according to a sensitivity set for the leakage current.

17. A vital sign measuring device comprising:

at least one light source that outputs an optical signal;

a sensing module that includes a pixel array including a plurality of unit pixels that detect a reflected optical signal reflected from an object to generate a pixel signal, and a pixel driving circuit that generates a vital sign of the object from the pixel signal; and a light shielding film that optically separates the sensing module from the at least one light source, wherein the sensing module detects a unit pixel group, among the plurality of unit pixels, in which a leakage current has occurred, and applies a control signal to deactivate the detected unit pixel group.

18. The vital sign measuring device according to claim 17, wherein the plurality of unit pixels are grouped by a predetermined unit into a plurality of pixel groups, wherein the sensing module determines whether the leakage current is generated for each of the plurality of pixel groups.

19. The vital sign measuring device according to claim 18, wherein the pixel array comprises, for each of the plurality of pixel groups, a comparator and a transistor, wherein the comparator compares an amplitude of a pixel signal obtained from the pixel group, with a reference voltage, and outputs a comparison signal to a gate of the transistor.

20. The vital sign measuring device according to claim 19, wherein the pixel array further comprises a current-voltage converter that is connected to an input terminal of the comparator and that converts the pixel signal obtained from the pixel group, into a voltage signal and outputs the converted voltage signal.

* * * * *